(12) United States Patent
Bukoski et al.

(10) Patent No.: US 6,184,254 B1
(45) Date of Patent: Feb. 6, 2001

(54) METHODS OF IDENTIFYING MODULATORS OF PERIVASCULAR SENSORY NERVE CA$^{2+}$ RECEPTORS

(75) Inventors: Richard D. Bukoski, Galveston; Ka Bian, League City, both of TX (US)

(73) Assignee: Board of Regents, The University of Texas System, Austin, TX (US)

( * ) Notice: Under 35 U.S.C. 154(b), the term of this patent shall be extended for 0 days.

(21) Appl. No.: 09/180,730

(22) PCT Filed: May 16, 1997

(86) PCT No.: PCT/US97/09097

§ 371 Date: Nov. 13, 1998

§ 102(e) Date: Nov. 13, 1998

(87) PCT Pub. No.: WO97/42951

PCT Pub. Date: Nov. 20, 1997

Related U.S. Application Data

(60) Provisional application No. 60/018,367, filed on May 16, 1996, now abandoned.

(51) Int. Cl.$^7$ .................. A01N 33/02; A61K 31/135; A61K 49/00; G01N 33/53
(52) U.S. Cl. .................. 514/653; 514/673; 514/674; 514/920; 514/930; 514/290; 424/9.2; 435/3; 435/7.1
(58) Field of Search .................. 514/920, 930, 514/290, 653, 673, 674, 654; 424/9.2; 435/3, 7.1

(56) References Cited

U.S. PATENT DOCUMENTS 4,761,417   8/1988  Maroko .

FOREIGN PATENT DOCUMENTS

| WO 93/04373 | 3/1993 | (WO) . |
| WO 94/18959 | 9/1994 | (WO) . |
| WO 95/11221 | 4/1995 | (WO) . |

OTHER PUBLICATIONS

Volpi et al Proc. Natl. Acad. Sci USA. 1981; 78(2), 795–799.*
Suzuki et al Am. J. Physiol. 242 (Heart Circ. Physiol. 11): H325–H336, 1982.*
Aalkjaer, et al., "Evidence for increased media thickness, increased neuronal amine uptake, and depressed excitation–contraction coupling in isolated resistance vessels from essential hypertensivies", Circ. Res., 61:181–186, 1987.
Andriantsitohaina, et al., "Evidence of neuropeptide Y on intracellular Ca hu 'and force development by isolated mesenteric resistance arteries, " J. Vascular Res., 30:309–314, 1993.
Bello–Reuss, et al., "The effect of acute unilateral and renal denervatio in the rat, " J. Clin. Invest. 56:208–217, 1975.
Bian and Bukoski, "Modulation of resistance artery force generation by extracellular Ca hu '", Am. J. Physiol. (Heart Circ. Physiol.), 269:h230–h238, 1995.
Bian and Bukoski, "Myofilament Ca hu 'sensitivity of normotensive and hypertensive resistance arteries", Hypertension, 25:110–116, 1995a.
Bohr, D.F., "Vascular smooth muscle: dual effect of calcium", Science, 19:597–599, 1963.
Brain, et al., "Calcitonin gene–related peptide is a potent vasodilator", Nature 313:54–56, 1985.

(List continued on next page.)

Primary Examiner—Diana Dudash
Assistant Examiner—Shahnam Sharareh
(74) Attorney, Agent, or Firm—Fulbright & Jaworski L.L.P.

(57) ABSTRACT

Methods of identifying compounds that relax or stimulate arterial tension through their action on perivascular sensory nerve calcium receptors are described. Compounds identified through such methods are useful for the treatment of hypertension, hypotension and other diseases and conditions that alter normal physiological blood pressure.

6 Claims, 18 Drawing Sheets

OTHER PUBLICATIONS

Brown, E.M., "Extracellular $Ca^2$ sensing, regulation of parathyroid cell function, and role of $Ca^2$, and other ions as extracellular (first) messengers", Physiol. Rev. 71:371–411, 1991.

Brown, et al., "Calcium –ion sensing cell–surface receptors", N. Engl. J. Med., 333:234–240, 1995.

Brown, et al., "Cloning and characterization of an extracellular $Ca^2$–sensing receptor from bovine parathyroid", Nature, 366:575–580, 1993.

Buccholz, et al., "Age–related changes in the sensitivity of sympathetic nerves to altered extracellular calcium in tail arteries of F–344 rats", Neurobiol. Aging, 15:197–201, 1994.

Bukoski, "Intracellular free $Ca^2$ in mesenteric resistance arteries and primary cultured myocytes of the spontaneously hypertensive and normotensive rats", J. Hypertension, 8:37–43, 1990.

Bukoski, et al., "Effect of $1,25(OH)_2$ vitamin $D_3$ and ionized $Ca^2$ on $^{45}Ca$ uptake by primary cultures of aortic myocytes of spontaneously hypertensive and Wistar–Kyoto normotensive rats", Biochem. Biopys. Res. Comm. 146:1330–1335, 1987.

Bukoski, et al., "Intracellular $Ca^2$ and force determined simultaneously in isolated resistance arteries", Am. J. Physiol. (Heart) 257:H1728–1735, 1989.

Bukoski, et al., "Intracellular $Ca^2$ and force generation determined in resistance arteries of normotensive and hypertensive rats", J. Hypertension, 12:15–21, 1994.

Bukoski, et al., "Mesenteric artery contractile properties during dietary calcium manipulation in spontaneously hypertensive Wistar Kyoto normotensive rats", Am. J. Hypertens. 2:440–448, 1989.

Bukoski, et al., "Vascular actions of calcium regulating hormones", Sem. Nephrol. 15(6):536–549, 1995.

Bukoskiand McCarron, "Altered aortic reactivity and lowered blood pressure associated with high $Ca^2$–intake in SHR", Am. J. Physiol., 251:H976–H983, 1986.

Burnstock and Ralevic, "New insights into the local regulation of bloof flow by perivascular nerves and endothelium", Br. J. Plastic Surg. 47(8):527–543, 1994.

Chen, et al., "Divalent cations suppress 3',5"–adenosine monophosphate accumulation by stimulating a pertussis toxin–sensitive guanine nucleotide–binding protein in cultured bovine parathyroid cells", Endocrinology, 123:233–239, 1989.

Cow, D., "Some reactions of surviving arteries", J. Physiol., xlii:125–143, 1911.

Croci, et al., "In vitro characterization of the non–peptide tachykinin NK1 and NK2–receptor antagonists, SR 140333 and SR48968 in different rat and guinea–pig intestinal segments", Life Sci. 56::267–275, 1994.

DiPette, et al., "Systemic and regional hemodynamic effects of calcium supplementation in mineralocorticoid–salt induced hypertension", Hypertension, 13:77–81, 1989.

Dockray, G.J., "Physiology of enteric neuropeptides", in: Physiology of the Gastrointestional Tract 3rd Edition, ed. by L. R. Johnson, Raven Press, NY. pp. 169–209, 1994.

Dominiczak and Bohr, "Cell membrane abnormalities and the regulation of intracellular calcium concentration in hypertension", Clin. Sci. 79:415–423, 1990.

Dominiczak and Bohr, "The primacy of the membrane microviscosity in genetic hypertension", Am. J. Hypertension, 4:963:969, 1991.

Du, et al., "Differential regulation of angiotensin II receptors in the rat kidney by low dietary sodium", Hypertension 25(2):872–877, 1995.

Dupont and Plummer, "Power and sample size calculations. A review and computer program", Controlled Clinical Trials, 11:116–128, 1990.

Edvinsson, et al., "Comparison of peptidergic mechanisms in different parts of the guinea pig superior mesenteric artery: immunocytochemistry at the light and ultrastructural levels and responses in vitro of large and small arteries", J. Automonic, Nerv. Sys. 28:141–154, 1989.

Folkow, B., "Physiological aspects of primary hypertension", Physiol. Rev., 62:347–504, 1982.

Fox, et al., "A first generation calcimimetic compound (NPS R–568) that acts on the parathyroid cell calcium receptor: a novel therapeutic approach for hyperparathyroidism", J. Bone Miner. Res., 8:S181 (Abstract), 1993.

Furchgott and Zawadzki"The obligatory role of endothelium cells in the relaxation of arterial smooth muscle by acetylcholine", Nature, 299:373–376, 1980.

Garrett, et al., "Calcitonin–secreting cells of the thyroid express an extracellular calcium receptor gene", Endocrinology, 136:5202–5211, 1995.

Garrett, et al., "Molecular cloning and functional expression of human parathyroid calcium receptor cDNAs", J. Biol. Chem. 270:12919–12925, 1995.

Hai, and Murphy "$Ca^2$, Cross–bridge Phosphorylation and Contraction", Ann. Rev. Physiol. 51:285–298, 1989.

Hatton and McCarron, "Dietary Calcium and Blood Pressure in Experimental Models of Hypertension. A Review", Hypertension 23(4):513–530, 1994.

Hollaway and Bohr, "Reactivity of vascular smooth muscle in hypertensive rats", Circ. Res. 33:678–685, 1973.

Holman, M.E., "Membrane Potentials Recorded with High–Resistance Micro–Electrodes; and the Effects of Changes in Ionic Environment on the Electrical and Mechanical Activity of the Smooth Muscle of the Taenia Coli of the Guinea–pig", J. Physiol. (Lond.) 141:464–488, 1958.

Holzer, et al., "Sensory neurons mediate protective vasodilation in rat gastric mucosa", Am. J. Physiol. 260:G363–G370, 1991.

Ignarro, et al., "EDRF generation and release from perfused bovine pulmonary artery and vein", Eur. J. Pharmacol 149:79–88, 1988.

Ishibashi, et al., "Differential expression and effect of calcitriol on myosin in the arterial tree", Am. J. Physiol: Cell Physiol. 269:C443–C450, 1995.

Jancso, et al., "Direct evidence for neurogenic inflammation and its prevention by denervataion and by pretreatment with capsaicin", Br. J. Pharmacol. 31:138–151, 1967.

Jones, A.W., "Altered ion transport in large and small arteries from spontaneously hypertensive rats and the influence of calcium", Circ. Res. (Suppl. 1):I277–I182, 1974.

Joshua et al., "The influence of extracellular $Ca^2$ on microvascular tone in the rate cremaster muscle", Proc. Soc. Exptl. Biol. Med. 189:344–352, 1988.

Kitazawa, et al., "G–protein–mediated $Ca^2$ sensitization of smooth muscle contraction through myosin light chain phosphorylation", J. Bio. Chem.266:1708–1715, 1991.

Kolaj, et al., "The opioid dynorphin modulates AMPA and kainate responses in acutely isolated neurons from dorsal horn", Brain Res. 671:227–244, 1995.

Kotecha and Neild, "Vasodilation and smooth msucle membrane potential changes in arterioles from the guinea–pig small intestine", J. Physiol. 482:661–667, 1995.

Li and Duckles, "Effect of age on vascular content of calcitonin gene–related peptide and mesenteric vasodilator nerve activity in the rat", Eur. J. Pharmacol., 236:373–378, 1993.

Li, J., et al., "Changes in extracellular $Ca^2$ over a physiologic concentration range differentially modulate reactivity of resistance arteries of spontaneously hypertensive and normotensive rats", Clin. Exp. Hyperten, 15(5):849–866, 1993.

Lindskog, et al., "The novel high–affinity antagonist, galantide, blocks the galanin–mediated inhibition of glucose–induced insulin secretion", Eur. J. Pharmacol. 210:183–188, 1992.

Maggi and Meli "The sensor–efferent function of capsaicin–sensitive sensory neurons", Gen. Pharmacol. 19:1–43, 1988.

McCarron, D.A., "Is calcium more important than soidum in the pathogenesis of essential hypertension?", Hypertension 7:607–627, 1985.

Miller and Scott, "The effect of perivascular denervation on endothelium–dependent relaxation to acetylcholine, Artery 17:233–247, 1990.

Missiaen, et al., "Calcium ion homeostasis in smooth muscle", Pharmac. Ther. 56:191–231, 1992.

Nemere, et al., "Nontranscriptional effects of steroid hormones", Receptor 3:277–291, 1993.

Nemeth and Scarpa, "Cytosolic $Ca^2$ and the regulation of secretion in parathyroid cells", FEBS Lett., 203:15–19, 1986.

Nemeth and Scarpa, "Rapid mobilization of cellular $Ca^2$ in bovine parathyroid cells evoked by extracellular divalent cations. Evidence for a cell surface calcium receptor", J. Biol. Chem. 262:5188–5196, 1987.

Nemeth, et al., "$Ca^2$ receptor–dependent regulation of cellular functions", NIPS 10: 1–5, 1995.

Okamura et al., "Neurogenic vasodilation in canine uteine and iliac arteries", J. Hypertension, 13:1163–1168, 1995.

Pollak, et al., "Mutations in the Humans $Ca^2$–sensing receptor gene causes familial hypocalciuric hypercalcemia and neonatal severe hyperparathyroidism", Cell 75(7):1237–1303, 1993.

Racke, et al., "Functional expression of the parathyroid of the parathyroid calcium receptor in Xenopus oocytes", J. Bone Miner. Res. 6:Suppl:S118, abstract, 1991.

Rapp and Demg, "Detection and positional cloning of blood pressure quantitative trait loci: is it possible?Identifying the Genes for Genetic Hyptenison", Hypertension 25(6):1121–1128, 1995.

Riccardi, et al., "Cloning and functional expression of a rat kidney extracellular calcium/polyvalent cation–sensing receptor", Proc. Natl. Acad. Sci. 92:131–135, 1995.

Rinaldi and Bohr, "Potassium–induced relaxation of arteries in hypertension: modulation by extracellular calcium", Am. J. Physiol. 256:H707–H712, 1989.

Rokaeus and Brownstein, "Construction of a porcine adrenal medullary cDNA library and nucleotode sequence analysis of two clones encoding a galanin precursor", Proc. Natl. Acad. Sci. 83:6287–6291, 1986.

Ruat, et al, "calcium sensing receptor: molecular cloning in rat and localization to nerve terminals", Proc. Natl. Acad. Sci., 92:3161–3165, 1995.

Rubino, et al., "Prejunctional modulation of sensory–motor nerve mediated vasodilation of the rat mesenteric arterial bed by adenosine", Eur. J. Pharmacol. 220:95–98, 1992.

Shoback, et al., "High calcium and other divalent cations increase inositiol trisphosphate in bovine parathyroid cells", Endocrinology 123:382–389, 1988.

Stull, et al., "Vascular smooth muscle contractile elements", Hypertension 17:723–732, 1991.

Vane, J.R., "The use of isolated organs for detecting active substances in the circulating blood", Br. J. Pharmacol. Chemother. 23:360–373, 1964.

Wang and Prewitt, "Captopril reduces aortic and microvascular growth in hypertensive and normotensive rats", Hypertension, 15:68–77, 1990.

Wang, et al., "Regulation of PDGF A: A possible mechanism for angiotensin II–induced vascular growth", Am. J. Physiol. 269:H356–H364, 1995.

Webb and Bohr, 37 Mechanism of membrane stabilization by calcium in vascular smooth muscle, Am. J. Physiol. 235:C227–C232, 1978.

Windholz, Ed., In: The Merck Index, an Encyclopedia of Chemicals, Drugs and Biologicals, Merck & Co., Inc., New Jersey, pp. 1261, Abstract No. 7946, 1983.

Wu, et al., "Mechanisms of calcium relaxation of vascular smooth muscle", Am. J. Physiol. H1411–H1416, 1991.

Yao, et al., "Heterogeneity of adenovirus–mediated gene transfer in cultured aortic and renal arteries of rats", Hypertension 26[part]: 1056–1050.

Zhang, et al., "Regulatin of vascular smooth muscle contraction–myosin light chain phosphorylatioin dependent and independent pathways", Can. J. Physiol. Pharmacol. 72: 1386–1391, 1994.

\* cited by examiner

Control

I-NAME

Spantide substance P neurokinin 1 and 2 angatonist 20 min capsaicin

METHODS OF IDENTIFYING MODULATORS OF PERIVASCULAR SENSORY NERVE $Ca^{2+}$ RECEPTORS

The present application claims the benefit of PCT/US97/09097, filed on May 16, 1997, which claims priority to U.S. Provisional Application No. 60/018,367, filed on May 16, 1996, now abandoned.

The government has rights to this invention because support for research was provided by NIH grant Nos. R29-HL41816 and NIH RO 1 -HL54901.

BACKGROUND OF THE INVENTION

1. Field of the Invention

The present invention relates generally to the fields of endocrinology and neurobiology. More particularly it concerns the mechanisms by which extracellular $Ca^{2+}$ and the steroid hormone 1,25 $(OH)_2$ vitamin $D_3$ modulate vascular smooth muscle force generation.

2. Description of Related Art

Essential hypertension is a major health problem in the U.S. with an estimated 50 million adults being affected (Gifford, 1993) and is characterized by an increase in peripheral resistance in the face of normal cardiac output (Folkow, 1982). There is a clear pattern of inheritance and influence of the environment (Lifton, 1996) and untreated hypertension is a significant risk factor for stroke, myocardial infarction, coronary artery disease, renal failure, and premature death (Gordon et al., 1977). Standard therapy is directed toward lowering blood volume (diuretics and salt restriction), or reduction of vascular tone (vasodilators, pressor antagonists, and sympatholytics) (The Fifth Report of the Joint National Committee on Detection, Evaluation, and Treatment of High Blood Pressure, 1993). Although medical management of hypertension has contributed to a large reduction in stroke incidence over the past two decades, reduction in risk of myocardial infarction has not shown a parallel improvement (Anderson et al., 1991). Thus, cardiovascular disease remains the number one cause of death in the U.S.

Available antihypertensive compounds have unwanted side effects or clear contraindications. Diuretics and beta adrenoreceptor antagonists are indicated as first line therapy (The Fifth Report of the Joint National Committee on Detection, Evaluation, and Treatment of High Blood Pressure, 1993) but are associated with significant untoward effects including erectile dysfunction and fatigue ($\beta$-blockers), and are contraindicated in renal failure (diuretics). These observations underscore the need for novel therapeutic approaches to hypertensive disease. One area of blood pressure research which has potential for the development of novel pharmacological strategies, but has remained untapped, is the study of the relationship between $Ca^{2+}$ homeostasis and blood pressure regulation.

Relationship Between Systemic $Ca^{2+}$ Homeostasis and Blood Pressure.

Evidence linking blood pressure and systemic $Ca^{2+}$ homeostasis includes the clinical observation that primary hyperparathyroidism is associated with hypertension and that parathyroidectomy frequently lowers blood pressure (Mallette et al., 1974; Massry et al., 1986), epidemiologic data associating regional hardness of water with death from cardiovascular disease (Sharrett and Feinleib, 1975), and Ayachi's seminal demonstration that elevated dietary calcium intake lowers blood pressure in the spontaneously hypertensive rat (SHR) (Ayachi, 1979) which has been amply confirmed (Arvola et al., 1993; Bukoski and McCarron, 1986; DiPette et al., 1989; Kageyama and Bravo, 1987; McCarron et al., 1981). Epidemiologic surveys (Ackley et al., 1983; Belizan and Villar, 1980; Fogh-Anderson et al., 1984; Garcia-Palmieri et al., 1984; Harlan et al., 1984; McCarron et al., 1982) and clinical trails (Bucher et al., 1996a; 1996b; Grobbee and Hofman, 1986; McCarron and Morris, 1985; Strazullo et al., 1986) also support a link between $Ca^{2+}$ intake and blood pressure in humans. For example, analysis of NHANES data showed a significant inverse correlation between blood pressure and calcium intake (McCarron and Morris, 1982); and surveys of pregnant women showed a correlation between gestational hypertension and calcium intake (Belizan and Villar, 1980; Bucher et al., 1996a). Although clinical trials have shown only a small overall blood pressure lowering effect of $Ca^{2+}$ supplementation (McCarron and Morris, 1985), subgroups have been shown to respond to $Ca^{2+}$ supplementation with a significant fall in blood pressure (Resnick et al., 1985a; 1985b).

Mechanisms Linking $Ca^{2+}$ Homeostasis with Blood Pressure.

Several hypotheses have been proposed to explain the apparent link between $Ca^{2+}$ homeostasis and blood pressure and have been recently reviewed (Bukoski et al., 1995). These include $Ca^{2+}$ induced modulation of calciotropic hormone levels, alterations in Na and water balance, or changes in sympathetic nerve activity. In contrast with these ideas, work in two areas has prompted proposal of a novel hypothesis which states that the perivascular CaR, acting as a sensor for extracellular $Ca^{2+}$, responds to changes in interstitial $Ca^{2+}$ concentration with the release of a local vasodilator substance. One area was the discovery that extracellular $Ca^{2+}$ relaxes isolated arteries at low physiologic concentrations (Bian et al., 1995); the other was the molecular demonstration of the parathyroid CaR (Brown et al., 1993b; Garrett et al., 1995c).

Modulation of Vascular Tone by Extracellular $Ca^{2+}$.

It has long been recognized that extracellular $Ca^{2+}$ can suppress arterial force generation (Bohr, 1963; Cow, 1911; Holman, 1958). The physiologic significance of this action of $Ca^{2+}$ has been unclear, however, since only very high concentrations of extracellular $Ca^{2+}$ have generally been shown to induce relaxation (Bohr, 1963; Hollaway and Bohr, 1973; Webb and Bohr, 1978). Recent work, however, has demonstrated that raising extracellular $Ca^{2+}$ from as little as 1.0 mM to 1.5 mM relaxes isolated arteries (Bian et al., 1995) and that cumulatively raising extracellular $Ca^{2+}$ above 1.5 mM causes nearly complete relaxation with an $ED_{50}$ value of 2.4±0.17 mM, n=12. Relaxation induced by $Ca^{2+}$ dependent on the release of an endothelium-derived relaxing factor, or on the production of NO, but is associated with the release of a vasodilator substance from the adventitial surface of the artery. These results, and observations that $Ca^{2+}$ induced relaxation is associated with decreased myofilament $Ca^{2+}$ sensitivity and can be blocked by $K^+$ channel antagonists led to the proposal that a $Ca^{2+}$ receptor that is similar or identical to that described in parathyroid gland plays a mediating role in contrast to persistent reports that the CaR is not expressed in vascular smooth muscle (Brown et al., 1993a; 1995).

$Ca^{2+}$ Homeostasis and Cell Function.

Serum ionized $Ca^{2+}$ is normally regulated within tight limits and is a function of the amount of $Ca^{2+}$ absorbed by the intestine, reabsorbed from the load filtered by the kidney, and the net sum of $Ca^{2+}$ deposition into and resorption from the bone mass. A simplified view of the endocrine mechanisms that regulate $Ca^{2+}$ homeostasis can be gained by considering the dynamic systemic responses that occur in response to changes in serum $Ca^{2+}$ (Bukoski et al., 1995). An increase in serum ionized $Ca^{2+}$ is recognized by the membrane spanning, G protein coupled CaR of the parathyroid cell which in turn elicits a decrease in the release of parathyroid hormone (PTH) (Brown et al., 1993a; 1995). The rise in $Ca^{2+}$ also activates a CaR on the thyroid C cell which increases calcitonin release (Garrett et al., 1 995a,b). A fall in serum $Ca^{2+}$ has the opposite effect of increasing PTH and decreasing calcitonin. PTH acts at the level of bone to increase release of $Ca^{2+}$ into the plasma, and the fall in calcitonin releases its suppressive effect on bone $Ca^{2+}$ resorption. PTH also acts as the kidney where it increases reabsorption of $Ca^{2+}$ and stimulates the production of 1,25 $(OH)_2$ vitamin $D_3$ which in turn acts via genomic and non-genomic mechanisms to increase intestinal absorption and renal reabsorption of $Ca^{2+}$ (Nemere et al., 1993). The net result is an increase in serum $Ca^{2+}$ at the expense of changes in calciotropic hormone levels.

Two important concepts for the working hypothesis are implicit in this model. One is that interfaces exist in the epithelial linings of the gut and kidney, and adjacent to metabolically active bone cells where gradients in interstitial $Ca^{2+}$ can be generated. The gradients expose adjacent tissues to levels of interstitial $Ca^{2+}$ that are significantly different from that which is present in the mixed venous plasma (e.g. serum ionized $Ca^{2+}$). This elevation in interstitial $Ca^{2+}$ may significantly modulate local cell function. The second concept is that changes in $Ca^{2+}$ ion content in the mixed plasma are of sufficient magnitude to stimulate $Ca^{2+}$ receptors on the parathyroid and thyroid C cells and to elicit changes in second messengers affecting PTH and calcitonin release. The CaR is therefore exquisitely sensitive to small, i.e., approximately 10th millimolar, changes in extracellular ionized $Ca^{2+}$.

The $Ca^{2+}$ Receptor (CaR).

It has recently been shown that parathyroid cells express a cell surface "$Ca^{2+}$ receptor" (CaR) which enables them to detect and respond to small changes in the concentration of extracellular $Ca^{2+}$ (Brown et al., 1993b). The parathyroid CaR is a G protein coupled receptor possessing a large extracellular domain and showing homology only with the metabotropic glutamate receptors. The parathyroid CaR is composed of 1078 amino acids in the human and 1079 in the rat and the native receptor is heavily glycosylated in both species. To date, only one gene for the CaR has been identified although there is some evidence for alternatively spliced forms and deletion/insertion mutations (Pollack et al., 1993). In an effort to explain high sensitivity $Ca^{2+}$-induced relaxation, it has been proposed that the CaR gene product may be present in the arterial wall (Bian et aL, 1995; Bukoski et al., 1995).

The discovery and molecular characterization of the $Ca^{2+}$ receptor was the culmination of studies of the cellular mechanisms by which extracellular $Ca^{2+}$ regulates the function of specific cell types, particularly the parathyroid cell. A breakthrough in this area was the cloning of cDNA encoding the CaR from the bovine parathyroid (Brown et al., 1993a). The coding region of the full length CaR cDNA is 3,237 bp and predicts a 120 kDa protein. This protein has 7 putative membrane spanning domains, intracellular protein kinase C phosphorylation sites, and a large extracellular domain with multiple glycosylation sites. The CaR has now been cloned from the human parathyroid (Garrett et al., 1995a,b), rat and human medullary thyroid carcinoma cell (Garrett et al., 1995a,b), rat kidney (Riccardi et al., 1995), and brain (Ruat et aL., 1995). Previously, attempts at localizing the CaR in the vascular wall, using northern blot analysis of aortic tissue, had failed to show the appropriate transcript.

Among the important pharmacologic properties of the CaR is the fact that it can be activated by polyvalent cationic molecules including the trivalent cations $La^{3+}$ and $Gd^{3+}$, neomycin, and spermine (Brown, 1991). This property led to the development of a novel class of phenylalkyamine derivatives by Nemeth and colleagues (1986; 1987; 1995). These compounds are the only potent and selective agonists that have been reported and are presently used in clinical trials for the treatment of hyperparathyroidism (Fox et al., 1993; Nemeth et al., 1995).

Recently is has been demonstrated that physiological levels of extracellular $Ca^{2+}$ significantly modulate force generation by resistance arteries (Bian et al., 1995a; 1995b). This observation, when coupled with independent observations that $Ca^{2+}$ in the interstitial space of tissues that are involved in transcellular $Ca^{2+}$ movement, i.e., the intestine, kidney, and bone, may be significantly greater than that which is present in the mixed venous plasma (Brown, 1991), provides a strong argument for the physiological significance of modulation of vascular tone by extracellular $Ca^{2+}$.

Modulation of Smooth Muscle Function by Extracellular $Ca^{2+}$.

It is well established that smooth muscle contraction is triggered by a rise in intracellular $Ca^{2+}$ which activates actomyosin ATPase through a myosin light chain phosphorylation dependent mechanism (Stull et aL, 1991). Although still controversial, it is also clear that steady state force maintenance is a $Ca^{2+}$ dependent process that depends upon either the formation of the latch bridge state (Hai et al., 1989) or a thin filament regulated mechanism (Zhang, et al., 1994).

Since a rise in intracellular $Ca^{2+}$ is critical for smooth muscle contraction, it is often assumed that extracellular $Ca^{2+}$ serves only as a storage reservoir for the transmembrane $Ca^{2+}$ gradient. Evidence that this is an oversimplification dates back to 1911 when Cow studied different mammalian arteries and showed that slightly supraphysiologic concentrations of $Ca^{2+}$ depress force generation (Cow, 1911). Approximately 50 years later, Bohr (1963) showed that $Ca^{2+}$ has a dual effect on smooth muscle; high concentrations of extracellular $Ca^{2+}$ suppress the early force response of the aorta to epinephrine, while the later steady state response is enhanced. This inhibitory effect of extracellular $Ca^{2+}$ was attributed to a "membrane stabilizing" effect and has been proposed to result from binding of $Ca^{2+}$ to the cell membrane surface which in turn decreases lipid bilayer mobility transmembrane $Ca^{2+}$ via transport proteins and channels (Dominiczak et al., 1990, Dominiczak et al., 1991).

Further characterization of the phenomenon of $Ca^{2+}$ induced relaxation showed that raising $Ca^{2+}$ from 4.1 to 20.1 mmol/L relaxes rat tail arteries (Webb et al., 1978); and the effect is antagonized by pre-treatment with ouabain, low Na, and low temperature. It was concluded that $Ca^{2+}$ induces relaxation by activating the Na pump. Wu and colleagues (1978) later showed that $K^+$-induced contraction of rat aorta is depressed as extracellular $Ca^{2+}$ from 0 to 5.1 mM caused a graded contraction in cremaster arterioles of the rat (Joshua et al., 1988).

Sensory Nerves and Vascular Reactivity

Primary sensory afferent nerves have cell bodies located in the dorsal root ganglia (DRG), synapse centrally in lamina I/II of the dorsal horn of the spinal chord, and send efferent processes to a variety of tissues including resistance arteries (Burnstock et al., 1994). Sensory nerves not only have an afferent sensory function whereby they send signals to the central nervous system, but they also have an efferent motor function on target tissues. This motor function can occur as an axon reflex, or by the release of a transmitter from the same terminal in response to environmental stimuli (Maggi et al., 1988).

Among the first pieces of information supporting a local sensory motor function was the observation that neurogenic inflammation can be prevented by denervation and desensitization by treatment with capsaicin (Jancso et al., 1967). This observation coupled with the knowledge that there is a complex pattern of peptide neurotransmitter distribution in the sensory nerve ending, including CGRP (Brain et al., 1985; Li, Y. et al., 1993), substance P (Burnstock et al., 1994; Edvinsson et al., 1989), neurokinin A (Croci et aL 1994; Edvinsson et al., 1989), galanin (Kotecha et al., 1995; Rokaeus et al., 1986), and dynorphin (Kolaj et al., 1995; Kotecha et al., 1995), led to the concept that local stimuli are capable of releasing vasoactive factors, which could then exert local effects. For example, it has been demonstrated that local sensory nerve release of vasodilators protects the gastric mucosa from injury by high concentrations of hydrogen ion by significantly increasing blood flow (Holzer et al., 1991). Thus, sensory nerves are in a position to monitor the interstitial environment and respond with the release of vasoactive chemicals. These can act directly on small arteries and arterioles or diffuse to the endothelium where they can induce release of vasoactive factors (Furchgott et al., 1980; Miller et al., 1990).

In summary the data suggest that the vessel wall is under the influence of local changes in cation content which in turn are linked with local metabolic and transport activities as well as whole animal mineral homeostasis. Thus it is possible that the CaR located on the perivascular sensory neurons associated with resistance arteries may provide a novel site of action for the discovery of drugs which may be used to alleviated hypertension and other diseases associated with altered blood pressure. However, currently no such method for identifying compounds which specifically modulate vasotension through action at the CaR has been developed.

SUMMARY OF THE INVENTION

The present invention seeks to overcome these and other drawbacks inherent in the prior art by providing novel methods for identifying compositions that modulate vascular tone by acting on $Ca^{2+}$ receptors of perivascular sensory nerves. Compounds that are identified by the described methods can be used to modulate the vascular tension and blood pressure of an animal. In certain embodiments, the identified compounds are useful to alleviate hypertension.

All of the methods disclosed herein are relevant to both medical and veterinary applications. Thus, the term "animal", as used throughout, includes human subjects and domestic, farm and zoo animals.

The invention provides methods which comprise contacting a mesenteric resistance artery freed of endothelial tissue with a compound and then measuring the arterial tension changes induced by the compound. Preferred compounds have vasodilator activity and release arterial tension as measured by contact of the mesenteric arteries,which have intact perivascular sensory nerve $Ca^{2+}$ receptors, with an effective level of extracellular $Ca^{2+}$.

The invention further provides that the tension-reducing action of compounds, that are identified as being capable of alleviating arterial tension, is reduced, or even obviated, in the tension assay when the mesenteric resistance arteries are pretreated with a blocker of $Ca^{2+}$ receptor-mediated relaxation.

In a further embodiment, the action of compounds which relax arterial tension, i.e. yield a positive result in the tension assay, is reduced, or even prevented, on mesenteric resistance arteries from animals subject to chronic sensory denervation by neonatal treatment.

The invention further provides that compounds identified as having (a) vasomodulating activity through the stimulation or inhibition of perivascular sensory nerve $Ca^{2+}$ receptors and (b) that such vasorelaxing activity is blocked from arteries of animals subject to sensory denervation are useful as vasorelaxation agonists which may be used to relieve or treat hypertension.

In one embodiment, the perivascular sensory nerve $Ca^{2+}$ receptor blocker is quinocrine.

In another embodiment the initially tested mesenteric resistance artery has been preconstricted and tension is relieved by the compound. Such identified compounds or compound may be used for the treatment of hypertension as a peripheral sensory nerve $Ca^{2+}$ receptor agonist.

In an alternative embodiment the mesenteric resistance arteries are not preconstricted and the compound causes constriction of the arteries or prevents relaxation of the arteries by exogenous $Ca^{2+}$. Such identified compounds or compound is a vasoconstrictor that may be used for the relief of hypertension.

In another aspect, the invention provides a novel method for the modulation of vascular tone comprising identifying a compound as a vasodilator or vasoconstrictor and administering a therapeutically effective dose of the compound to a patient.

In still another aspect, the invention provides a method of treating a patient for hypertension comprising identifying a vasodilator and administering a therapeutically effective level of the vasodilator to a hypertensive patient.

Compounds identified by the screening methods described herein are envisioned to be useful as a vasodilators for relief of angina, used in the treatment of coronary vasospasm, used as a vasodilators in reperfusion of ischemic myocardial tissue, used in protecting areas of the brain that are in the penumbra of a ischemic zone following stroke, used in preventing vasospasm occurring several days after cerebrovascular accidents; used in restoring normal vascular reactivity to the brain after traumatic brain injury; useful in the treatment of spastic colon, the management of intestinal cramping associated with inflammatory bowel disease, the protection of gastric mucosa by enhancing mucosal blood flow during acid secretion and the enhancement of absorption of nutrition; useful in the treatment of impotence associated with vascular dysfunction and management of urinary incontinence; PvSN antagonists can be useful for modulation of local inflammation response and modulation of the chronic pain transmission with indication for symptomatic treatment of arthritis; useful for the treatment of diabetic vascular injury associated with degenerative perivascular nerve function; useful for the treatment of premenstrual uterine cramping, treatment of pregnancy-induced hypertension, treatment of preeclampsia and treatment of cessation of premature labor with benefit to fetus and mother; used for the preservation of renal function through a vasodilator effect; and useful for the treatment of bronchospasm and reactive airway disease.

DESCRIPTION OF THE DRAWINGS

FIG. 6A. Control indicates control response of the vessel to cumulative addition of $Ca^{2+}$ from 1 mmol/L to 1.5, 2, 3, 5, 7.5, and 10 mmol/L. A downward deflection indicates a relaxation of the artery. FIG. 6B. L-NAME indicates the effect of pre-treatment of the vessel with 100 $\mu$mol/L L-NAME to inhibit nitric oxide synthase activity. FIG. 6C. Spantide indicates the effect of blockade of neurokinin 1 and neurokinin 2 receptors by pretreatment with 10 $\mu$mol/L of spantide which is a substance P antagonist. FIG. 6D. The effect of a 20 minute treatment of the vessel with 10 $\mu$mol/L capsaicin, which is a specific sensory nerve blocker.

DESCRIPTION OF ILLUSTRATIVE EMBODIMENTS

Figure 1:
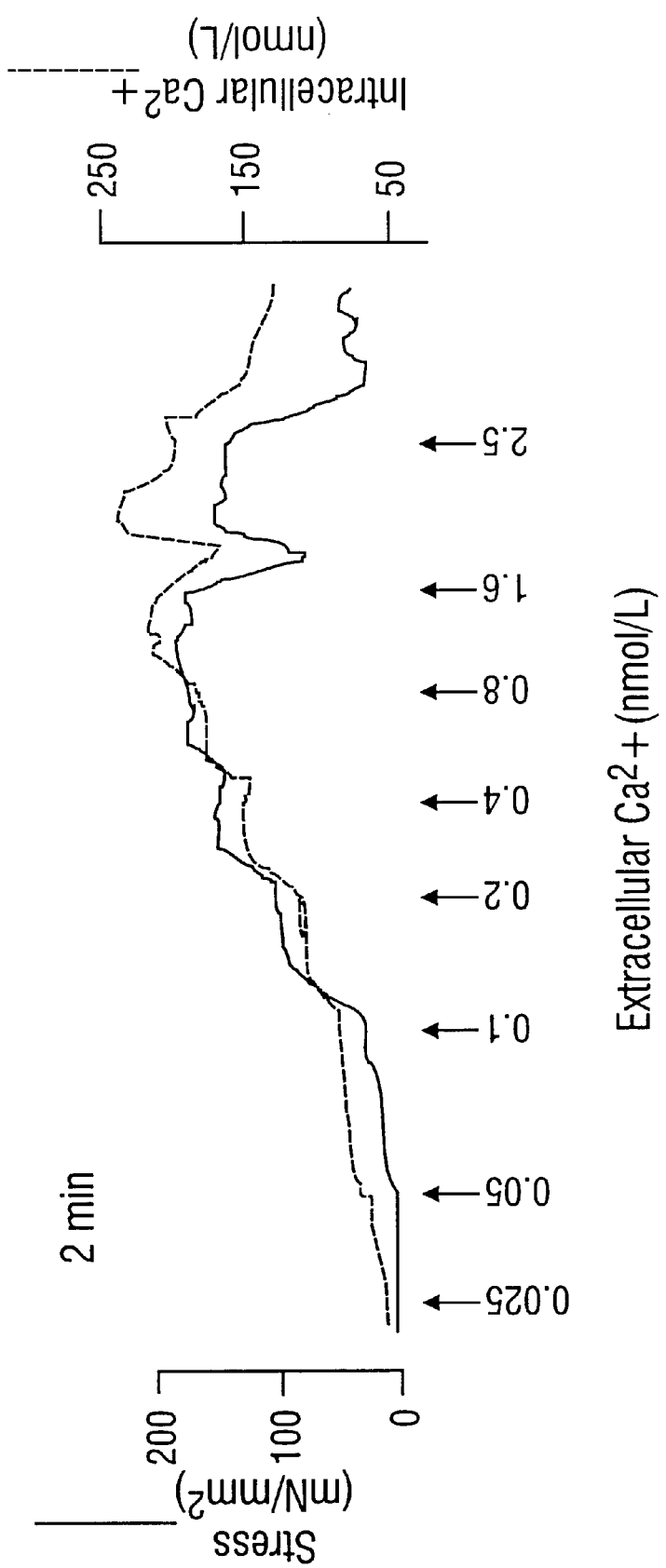
FIG. 1. Isometric force and intracellular $Ca^{2+}$ response of a mesenteric resistance arteries to increasing extracellular $Ca^{2+}$ in the presence of 10 $\mu$M norepinephrine. Vessel segment was depleted of $Ca^{2+}$ by repeated exposure to NE in $Ca^{2+}$-free PSS prior to addition of $Ca^{2+}$. Note decrease in force and $Ca^{2+}$ upon increasing $Ca^{2+}$ from 0.8 to 1.6 and from 1.6 to 2.5 mM (Bian et al., 1995b).

The invention comprises a means of determining whether a compound relaxes via stimulation of the perivascular sensory nerve $Ca^{2+}$ receptor (CaR) or via another unrelated mechanism. The assay is intended to be used as a secondary screen to determine whether $Ca^{2+}$ receptor agonists that have been identified using a high through-put primary screen should be moved into more time-consuming and expensive low through-put tertiary screens to determine whether they modulate cardiovascular function. It is envisioned that lead compounds or structural analogs of lead compounds will be tested in an in vitro expression system to determine whether they are high potency activators of the sensory nerve CaR. Compounds which are judged as "hits" will then be moved onto the secondary screen.

This secondary screening allows the rapid identification of $Ca^{2+}$ receptor agonists which relax isolated arteries through an action on the perivascular sensory nerve network. Compounds that are identified as active in this secondary screen are then moved into the more time-consuming in vivo assay for characterization of their effects on cardiovascular properties including blood pressure, heart rate and regional vascular resistance. The assay thus serves as a means of reducing the time and expense required for identification of $Ca^{2+}$ receptor agonists with blood pressure lowering properties.

It is clear that force generation, intracellular $Ca^{2+}$ handling, and myofilament $Ca^{2+}$ sensitivity are not altered in isolated resistance arteries of the SHR strain of genetically hypertensive rats (Bian et al., 1995a, Bukoski et al., 1987, Bukoski, 1990, Bukoski et al., 1994). These observations are inconsistent with a body of data which show that peripheral resistance and in vivo reactivity are clearly enhanced (Folkow, 1982). This apparent conflict, combined with the fact that chronic changes in dietary $Ca^{2+}$ intake do not cause alterations in vascular reactivity in subsequently isolated arteries, led to the hypothesis that changes in the ionic content of interstitial fluid may occur in hypertension and that such alterations may significantly modulate regional vascular tone. Therefore studies were initiated to determine whether small, physiologic changes in extracellular $Ca^{2+}$ have the ability to alter vascular smooth muscle force generation.

The present invention shows that while original reports were correct in concluding that the CaR is not present in vascular smooth muscle (Brown et al., 1993a; 1995), it is present in the perivascular sensory nerve (PvSN) network of small resistance arteries. The data supplied herein thus constitutes the first localization of the CaR to the cardiovascular system and this newly discovered site of action provides the basis for the development of the novel methods of identifying potential agonists of hypertension that are disclosed herein.

The present discovery of the PvSN CaR system is of major significance for several reasons. First, it provides a unique molecular mechanism by which alterations in whole body $Ca^{2+}$ and $Na^+$ homeostasis can be coupled to vascular resistance and blood pressure regulation. Second, it provides the first cardiovascular target for the class of $Ca^{2+}$ receptor activating "calcimimetic" compounds. Third, it significantly expands the knowledge base of the mechanisms that modulate vascular reactivity in health and disease.

The inventors have discovered that extracellular $Ca^{2+}$ altered over a physiologic concentration range, reproducibly relaxes small resistance arteries of the rat. It is postulated that the $Ca^{2+}$-induced relaxation is mediated by activation of membrane spanning $Ca^{2+}$ receptors expressed in sensory efferents of the perivascular nerve network which induce the release of vasodilator neuropeptide that either acts directly on the smooth muscle cell to cause relaxation or stimulates the endothelium to release a relaxing factor [nitric oxide (NO) or endothelium-derived hyper polarizing factor (EDHF)].

This discovery provides the logical rationale for pharmacologically or chemically manipulating the activity of the perivascular sensory nerve $Ca^{2+}$ receptor as a means of increasing or decreasing vascular reactivity. For example, the perivascular sensory nerve $Ca^{2+}$ receptor can be targeted for the development of pharmacologic compounds that modulate $Ca^{2+}$ receptor activity with the therapeutic goal of treating cardiovascular diseases in the human. Diseases which could be treated include arterial hypertension, ischemic heart disease, coronary vasospasm, reperfusion of organs including heart, brain, kidney after ischemic events, and control of vasospasm in cerebral arteries after brain hemorrhage or trauma.

In addition to manipulation of the perivascular $Ca^{2+}$ receptor by pharmacologic compounds, it is envisioned that this system is a useful target of diet-related therapies which could activate the system in a natural way with few if any untoward effects such that hypertension is reduced or other diseases are alleviated.

This discovery entails the identification of the $Ca^{2+}$ receptor in the perivascular nerve network and provides for the first time the molecular basis by which $Ca^{2+}$ in the interstitial space can modulate vascular reactivity, and by which drugs that activate or suppress the $Ca^{2+}$ receptor may be designed for use in the regulation of the cardiovascular function. It is envisioned that this discovery coupled with the novel methods described herein permit the development and identification of new anti-hypertensive drugs.

The broadest applications of this discovery extend to all systems that are innervated by the sensory nervous system and in addition to functions of the cardiovascular system, would include nocioception and pain transmission in conditions such as arthritis. Thus, the boundaries of this invention extend beyond the cardiovascular system.

Moreover this invention is not limited to identifying compounds which only act on PvSN CaR, as the $Ca^{2+}$ receptor/sensory nerve unit may be functional in other smooth muscles (such as tracheal muscle, intestinal muscle, uterine muscle). The broadest applications of the discovery include all biological systems innervated by the sensory nerves. An important concept which forms the basis of this claim is that in addition to their primary afferent sensory function, axons extending from the dorsal root ganglia have an efferent sensory motor function in which local nerve processes release transmitter at effector tissues in response to both electrical stimulation and in response to local chemical stimuli. Thus, smooth muscles of all types that receive sensory innervation are potential targets; including airway muscle, uterine muscle, the bladder, and the gastrointestinal tract. It is envisioned that the novel methods described herein can be used to identify compounds that target neural CaR such that they modulate bronchial constrictor activity in reactive airway disease, disorders of intestinal motility in conditions such as spastic colon and inflammatory bowel disease, and abnormal uterine contractibility that could result in premenstrual cramping in the non-pregnant female or premature delivery of the fetus in the pregnant female.

There are presently a large number of compounds that have been approved for treatment of hypertension and they can be divided into 8 or 9 major classes (Table 1). Of these, however only four are recommended for first line therapy of hypertension and all have specific contraindications and significant side effects which interfere with patient compliance. In addition, there is concern in the hypertension community regarding the fact that although blood pressure control has been available for several decades and there has been a significant (50%) reduction in morbidity and mortality from stroke, a similar magnitude of improvement in risk of cardiovascular events associated with coronary artery has not been observed. Moreover, none of the current compounds have the potential to combine antihypertensive properties with positive effects on $Ca^{2+}$ homeostasis and bone health and could be targeted toward an increasingly aged population.

TABLE 1

Major classes of drugs for treating hypertension.

| Class | 1st line therapy | contraindications or side effects |
|---|---|---|
| diuretics | yes | yes |
| β blockers | yes | yes |
| ACE inhibitors | yes | yes |
| $Ca^{2+}$ channel antagonists | yes | yes |
| vasodilators | no | yes |
| sympatholytics | no | yes |
| α-antagonists | no | yes |
| Ang II receptor antagonists | no | yes |
| $K^+$ channel agonists | no | yes |

Another attractive feature of this discovery is that it provides a molecular mechanism for linking disturbances in cation ($Ca^{2+}$ and $Na^+$) homeostasis with blood pressure control. Thus PvSN CaR agonists may exert specific beneficial effects on blood pressure in a major sub-group of human hypertensives, namely low renin, salt sensitive individuals that have been described and are reported to be responsive to dietary $Ca^{2+}$ supplementation. In addition, if one considers that gene polymorphism in the PvSN CaR contributes to the altered cation homeostasis and elevated blood pressure of these individuals, then a genetic screening assay could be developed and marketed which would allow diagnosis of this subclass of individuals and at risk offspring/siblings and would provide appropriate direction for rational development of therapeutics strategies.

In addition to traditional schemes for targeting delivery to specific organs or tissues, there is another means of achieving specificity/selectivity of the PvSN CaR agonists. This is based on the possibility that the neurotransmitter which is released upon activation of the PvSN CaR varies from tissue to tissue or from regional circulation to regional circulation. Thus, activation of the PvSN in one tissue may elicit the release of one type of vasoeffector molecule such as CGRP while in another tissue it elicits the release of another such as nitric oxide or a hyperpolarizing factor. Thus it should be possible to affect vascular tissue without provoking responses in the gut or airway and vice versa.

The present invention involves the discovery that an extracellular $Ca^{2+}$ receptor is located in the perivascular sensory nerve network and that activation of this receptor with $Ca^{2+}$ results in the release of vasodilator neurotransmitter which either directly relaxes smooth muscle or elicits the release of endothelium derived relaxing factors, e.g., NO or and EDHF. Messenger RNA for the CaR is present in kidney (used as a positive control), and dorsal root ganglia (DRG) which house cell bodies of the sensory neurons. Messenger RNA was not detected in the heart, aorta, or mesenteric resistance artery. Native $Ca^{2+}$ receptor protein migrating as multiple bands between 120 and 160 kDa protein is present in both thyroparathyroid and mesenteric artery samples. An immunoreactive band migrating at 70 kDa was identified by microsequence analysis as rat albumin. Examination of the $Ca^{2+}$ receptor in perivascular nerve network by immunostaining determined the presence CaR immunoreactivity in fine adventitial nerve network and that CaR immunoreactivity is absent in the muscular media.

FIGS. 6A–6D illustrate that $Ca^{2+}$ induces relaxation of resistance arteries over a physiologic concentration range, and that the relaxation is inhibited/reversed by 20 minutes pre-treatment with 10 μM capsaicin, and by 100 μM L-NAME. Control (FIG. 6A) indicates control response of the vessel to cumulative addition of $Ca^{2+}$ from 1 mmol/L to 1.5, 2, 3, 5, 7.5, and 10 mmol/L. A downward deflection indicates a relaxation of the artery. L-NAME (FIG. 6B) indicates the effect of pre-treatment of the vessel with 100 μmol/L L-NAME to inhibit nitric oxide synthase activity. Spantide (FIG. 6C) indicates the effect of blockade of neurokinin 1 and neurokinin 2 receptors by pretreatment with 10 μmol/L of spantide which is a substance P antagonist. Twenty minutes capsaicin (FIG. 6D) indicates the effect of a 20 minute treatment of the vessel with 10 μmol/L capsaicin, which is a specific sensory nerve blocker.

Figure 7:
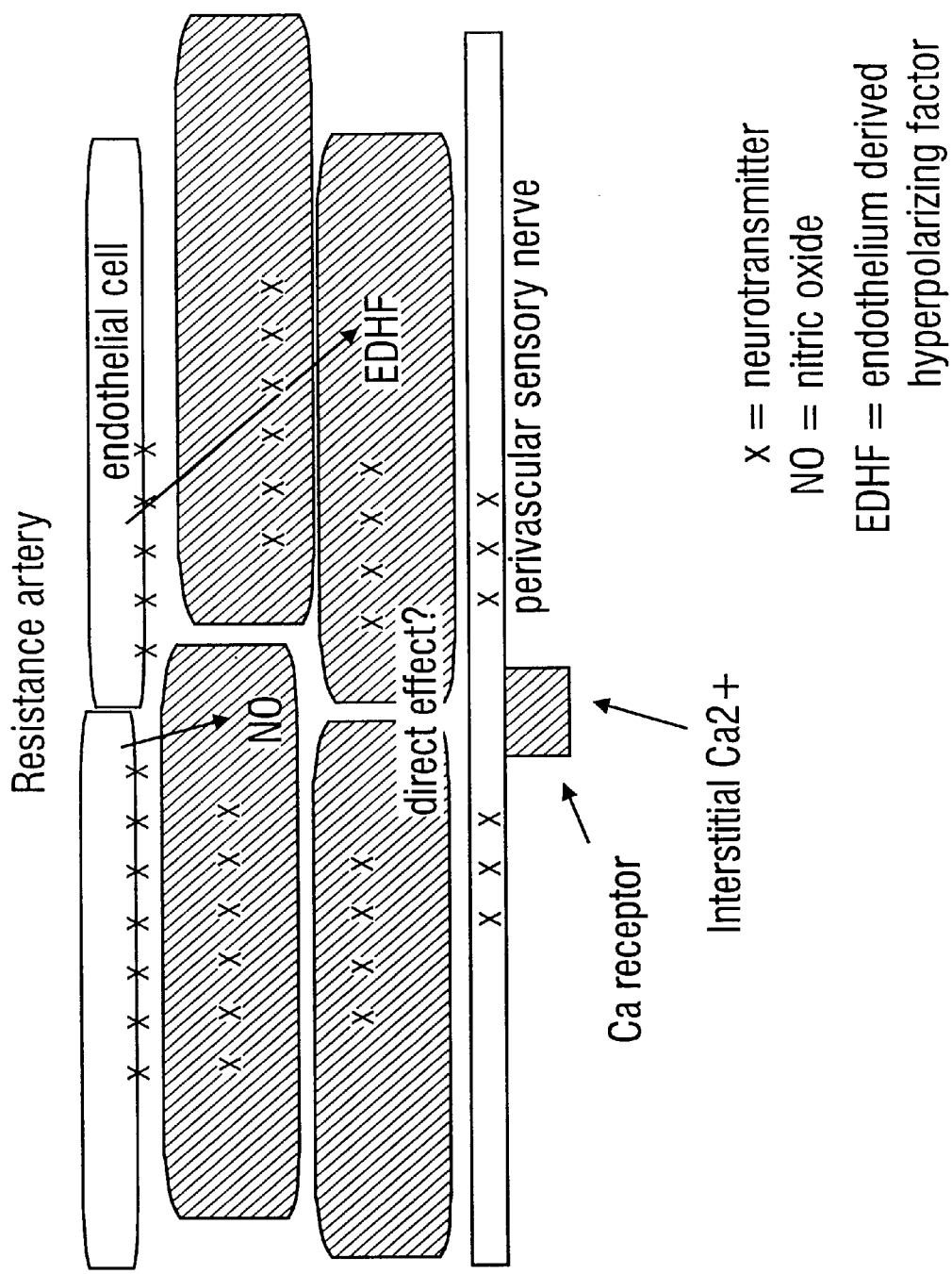
FIG. 7. A model demonstrating the hypothetical mechanism by which activation of the $Ca^{2+}$ receptor located in the sensory nerve network induces relaxation. An increase of $Ca^{2+}$ within the interstitial space activated a $Ca^{2+}$ receptor located on the perivascular neuron which indices that release of neurotransmitter which is denoted as "x". The neurotransmitter can either then act on the smooth muscle cell (stippled areas in center) and induce direct vasodilation or diffuse to the endothelial layer where it elicits the release of an endothelium derived relaxing factor, nitric oxide (NO) and/ or a hyperpolarizing factor. The latter is supported by the observation that the relaxation induced by $Ca^{2+}$ is blocked by $K^+$ channel inhibition.

FIG. 7 is a diagram outlining the proposed mechanism by which activation of the $Ca^{2+}$ receptor, using either $Ca^{2+}$ as a ligand or a specific $Ca^{2+}$ mimetic drug, dilates vascular smooth muscle. An increase of $Ca^{2+}$ within the interstitial space activated a $Ca^{2+}$ receptor located on the perivascular neuron which indices that release of neurotransmitter which is denoted as "x". The neurotransmitter can either then act on the smooth muscle cell (stippled areas in center) and induce direct vasodilation or diffuse to the endothelial layer where it elicits the release of an endothelium derived relaxing factor, nitric oxide (NO) and/or a hyperpolarizing factor. The latter is supported by the observation that the relaxation induced by $Ca^{2+}$ is blocked by $K^+$ channel inhibition. This system could readily be adapted for use in compound screening in a drug discovery program aimed at devising new antihypertensive vasodilator drugs or for the other therapeutic uses outlined above.

Figure 8A:
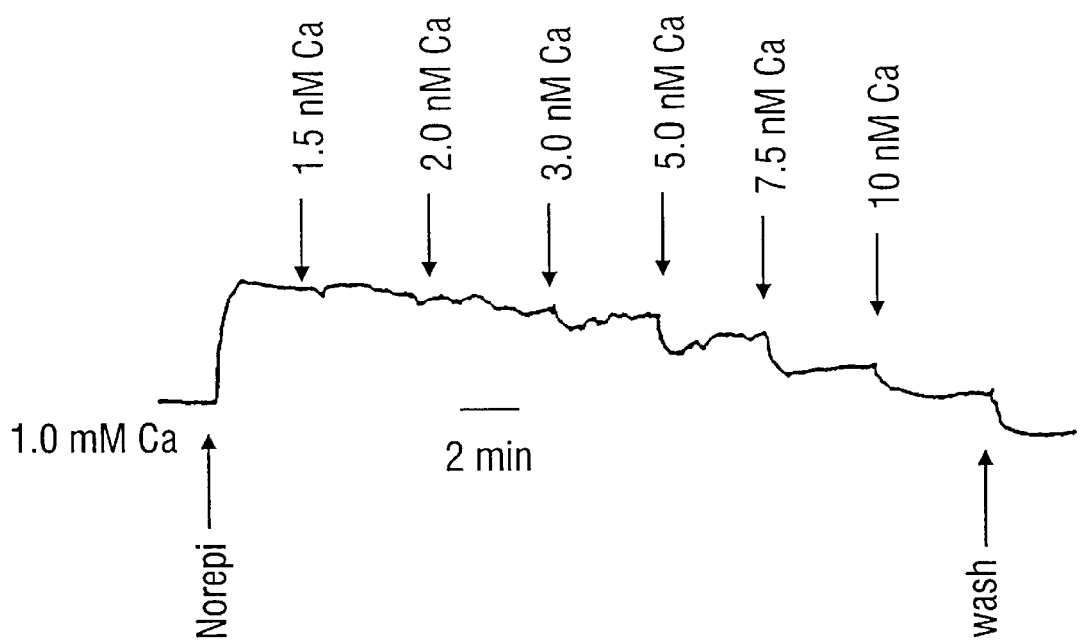
FIG. 8A. Representative trace of the active force response of a mesenteric resistance artery precontracted with norepinephrine to cumulative addition of extracellular $Ca^{2+}$.
Figure 8B:
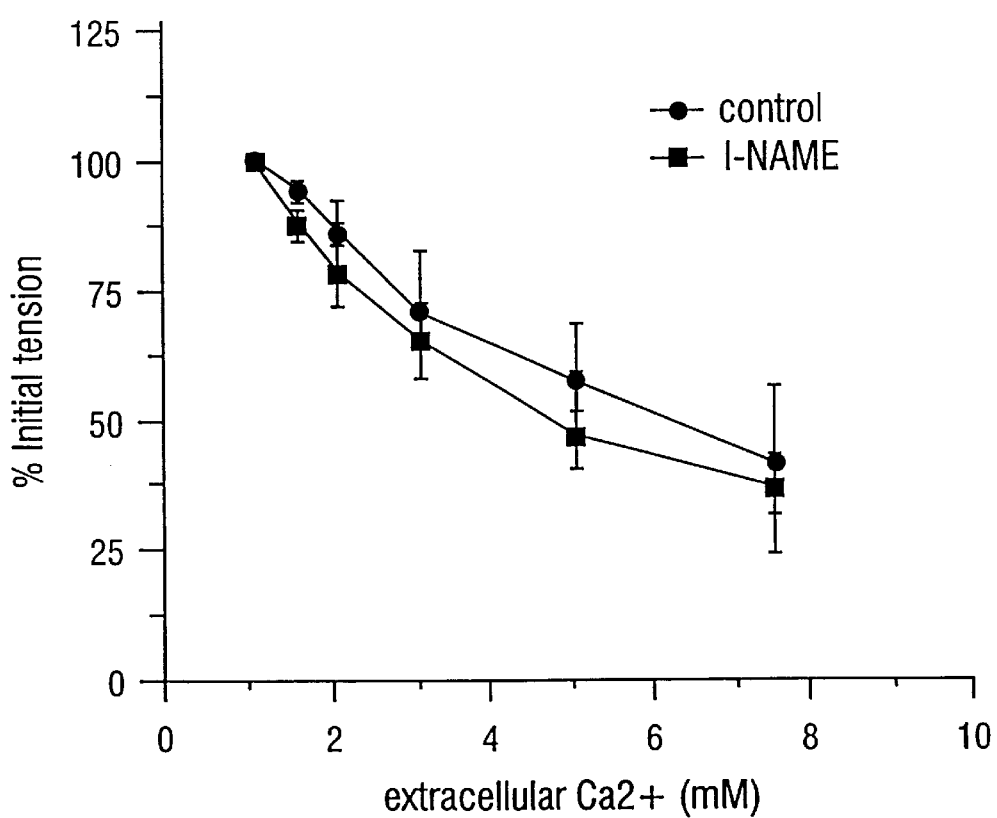
FIG. 8B. Line graph illustrating the mean responses of vessels under control conditions (open square with dot) and after pre-incubation with 0.1 mM L-NAME to inhibit nitric oxide synthase activity.
Figure 8C:
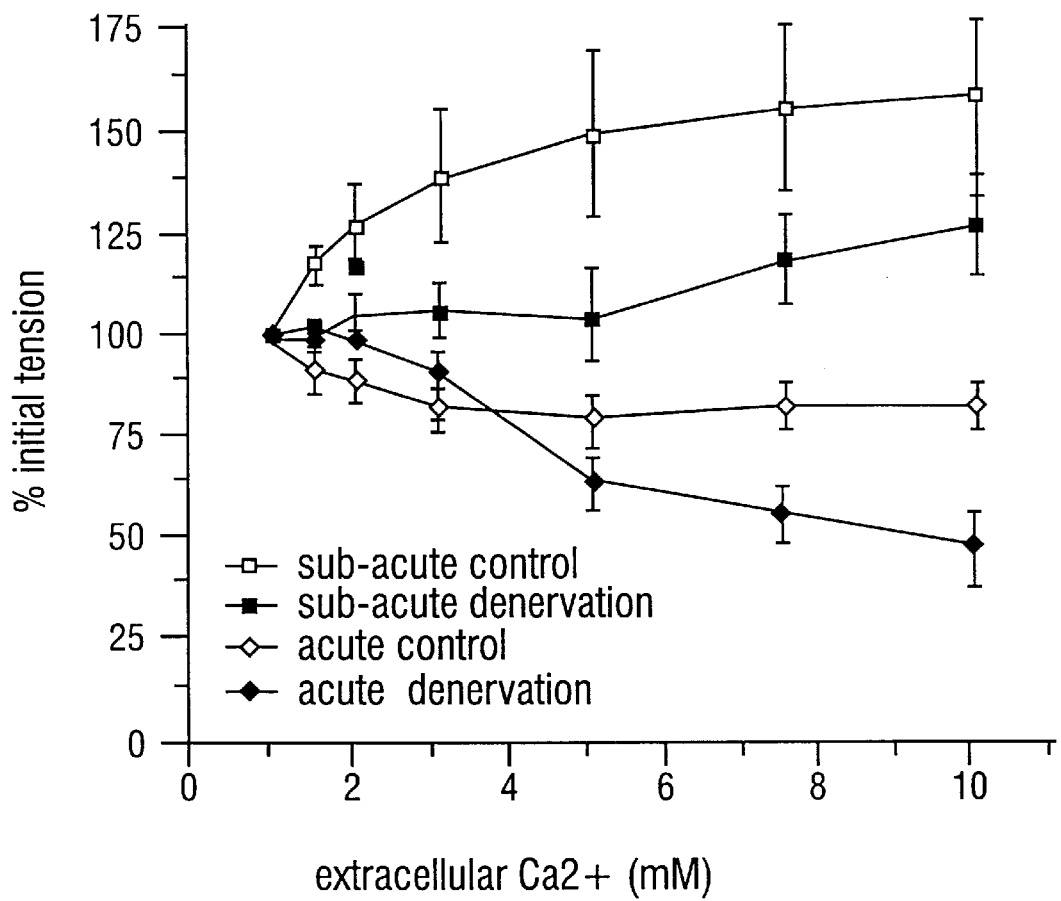
FIG. 8C. The effect of acute denervation by topical application of 0.75% phenol to isolated segments on $Ca^{2+}$-induced relaxation (n=4, p=0.007); and sub-acute denervation (n=4, p=0.026).
Figure 9A:
FIG. 9A. Shows a response of renal artery segment pre-contracted with norepinephrine (NE) to cumulative addition of $Ca^{2+}$ (note absence of response to 5 mM $Ca^{2+}$).
Figure 9B:
FIG. 9B. Response of same renal artery to solution of the indicated composition that was first allowed to superfuse over an arcade of mesenteric resistance arteries (note relaxation response to the mesenteric superfusate containing 5 mM $Ca^{2+}$).
Figure 9C:
FIG. 9C. Response of the same renal artery segment, now pre-contracted with NE to the cumulative addition of $Ca^{2+}$ and to the direct addition of the mesenteric superfusate collected during the relaxation induced by 5 mM $Ca^{2+}$ in FIG. 9B; similar results were observed in vessels isolated from three separate rats.
Figure 10:
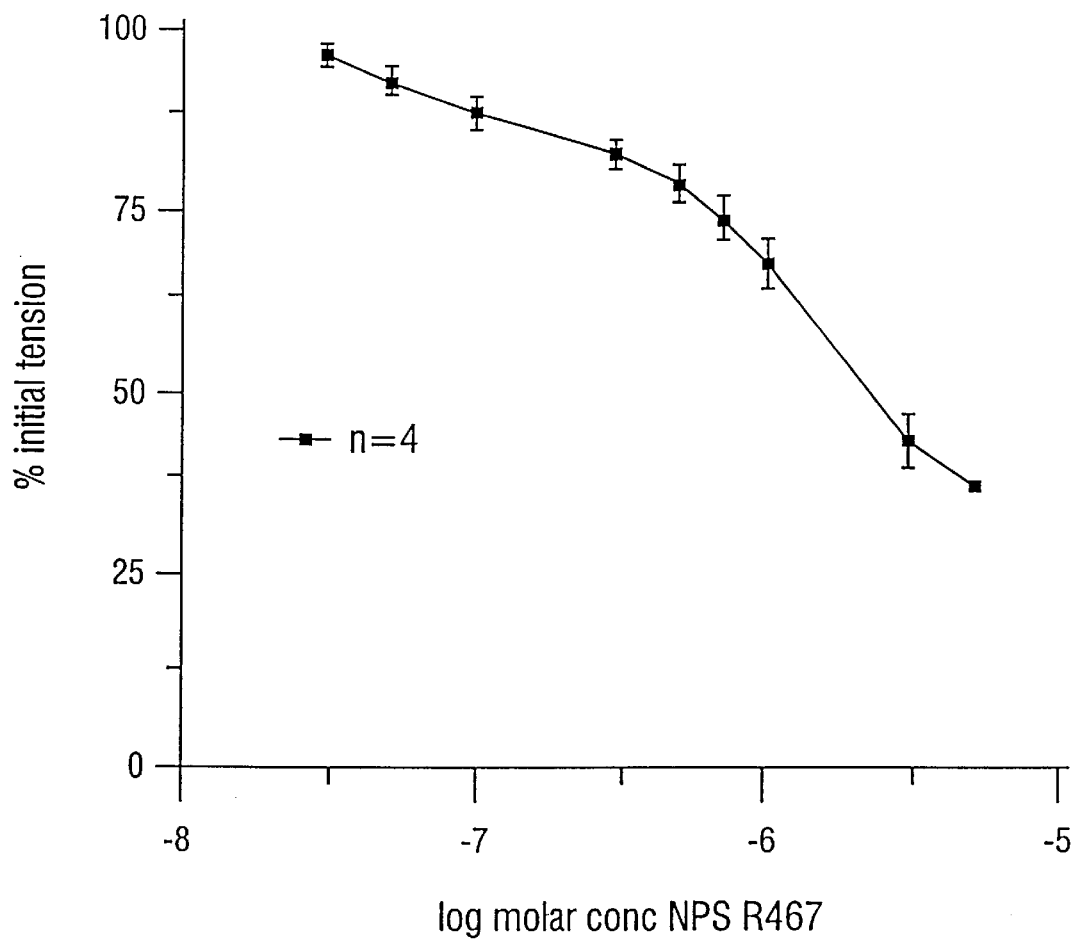
FIG. 10. The effect of NPS R467 on mesenteric resistance artery.

The invention is exemplified by a bioassay that is designed to take advantage of the fact that segments taken from the main renal artery do not relax in response to the direct addition of $Ca^{2+}$, as shown in FIG. 8, which was used to examine the hypothesis that $Ca^{2+}$ elicits the release of a diffusible relaxing substance from the adventitial surface of mesenteric resistance arteries. The renal artery used as the bioassay segment was isolated and mounted between a fixed support and a force transducer and the lack of response to addition of $Ca^{2+}$ was verified (FIG. 9A). The bioassay segment was then superfused with PSS that was allowed to drip across a mesenteric arcade attached to PE-10 tubing; the cut ends of the arcade were tied with suture material to prevent egress of endothelium-derived factors. Five millimolar $Ca^{2+}$, which was without effect when added directly to the bioassay vessel (FIG. 9A), caused relaxation of the bioassay segment when first superfused over the donor segment (FIG. 9B). To further examine the possibility that a diffusible substance was released from the mesenteric arcade in response to 5 mM $Ca^{2+}$, the superfusate was collected and stored on ice for approximately 45 minutes. The bioassay segment was then returned to the organ chamber, recontracted with norepinephrine and the response to $Ca^{2+}$ and to the collected superfusate were assessed. $Ca^{2+}$ (1.5–5.0 mM) had no effect on the vessel whereas the superfusate, at a dilution of 1:10) induced a sustained relaxation (FIG. 9C). These results prove that $Ca^{2+}$ elicits the release of a diffusible vasodilator substance.

Figure 4A:
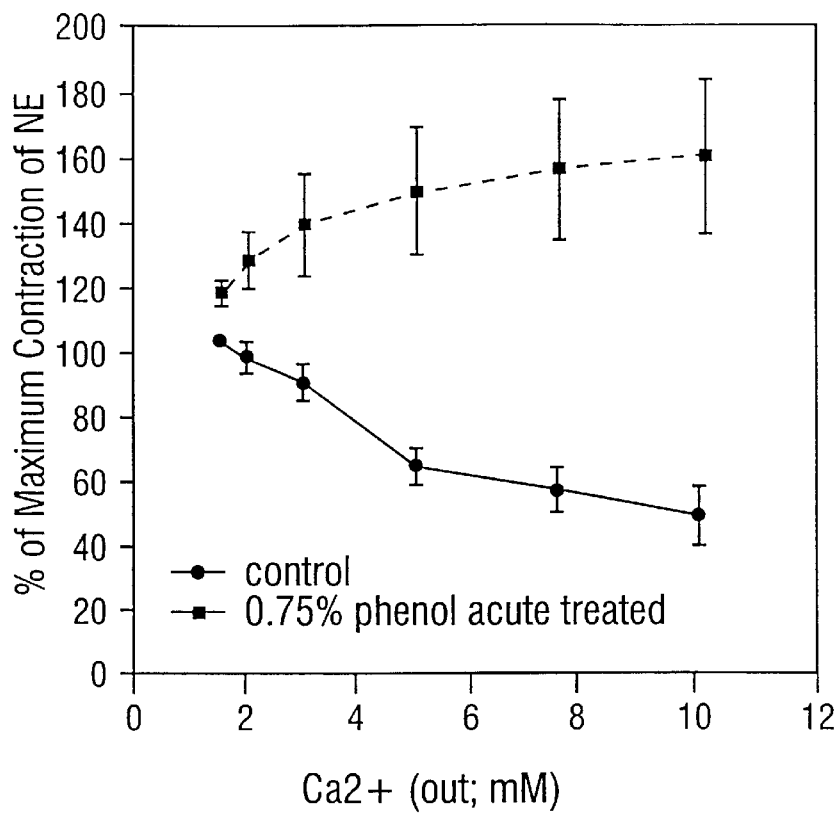
FIG. 4A. Demonstration that acute addition of 0.75% phenol, which destroys perivascular nerves, completely inhibits of $Ca^{2+}$-induced relaxation of mesenteric resistance arteries.
Figure 4B:
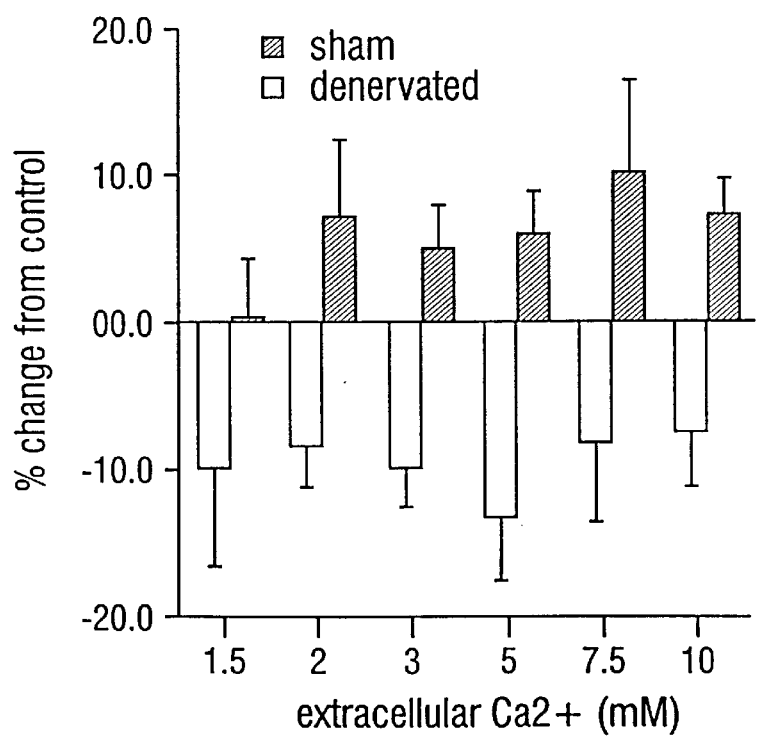
FIG. 4B. Demonstration that sub-acute denervation by in vivo application to 10% phenol to the mesenteric vasculature inhibits $Ca^{2+}$-induced relaxation.
Figure 5:
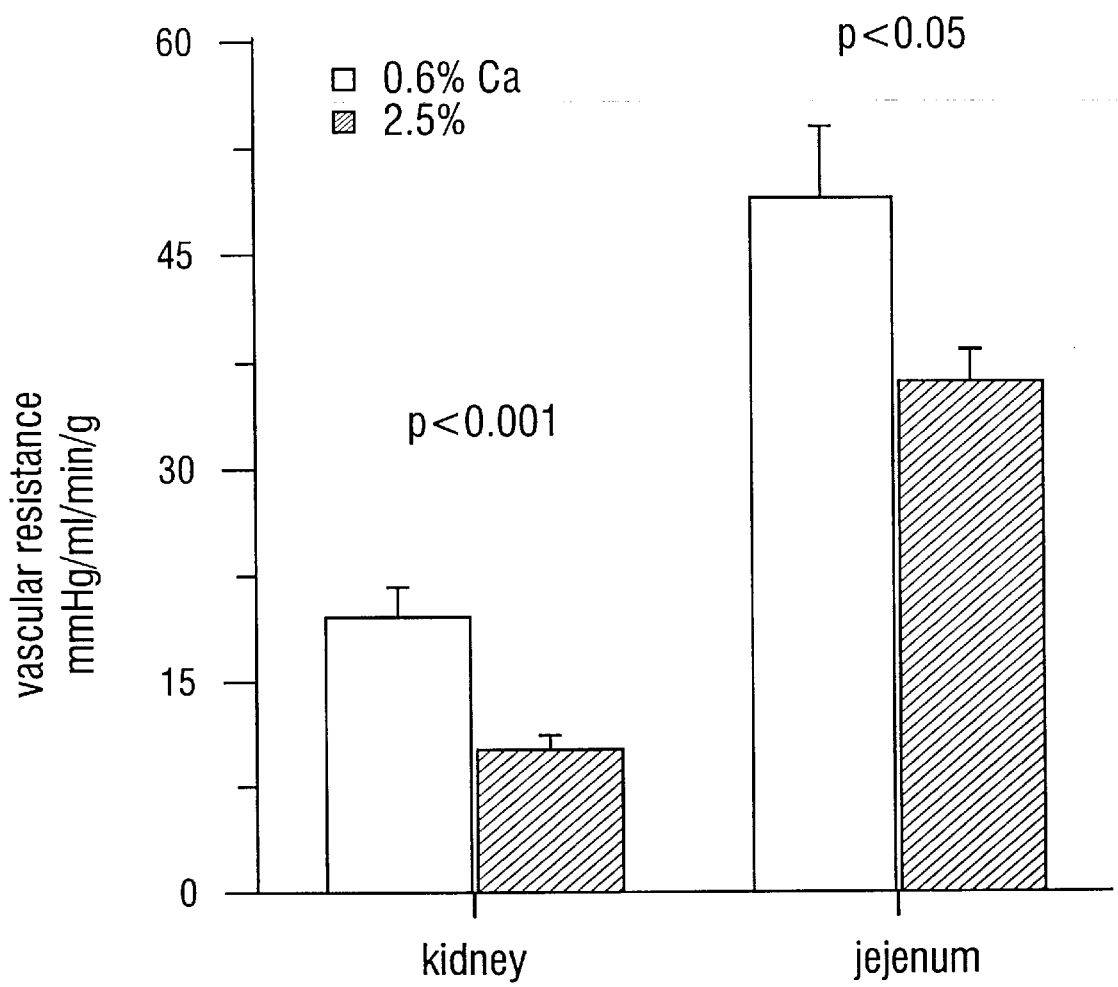
FIG. 5. The effect of dietary $Ca^{2+}$ (0.6% vs 2.5%) on regional blood flow in DOC salt hypertensive rats determined using the radioactive microsphere technique (DiPette et al., 1989).
Figure 6A:
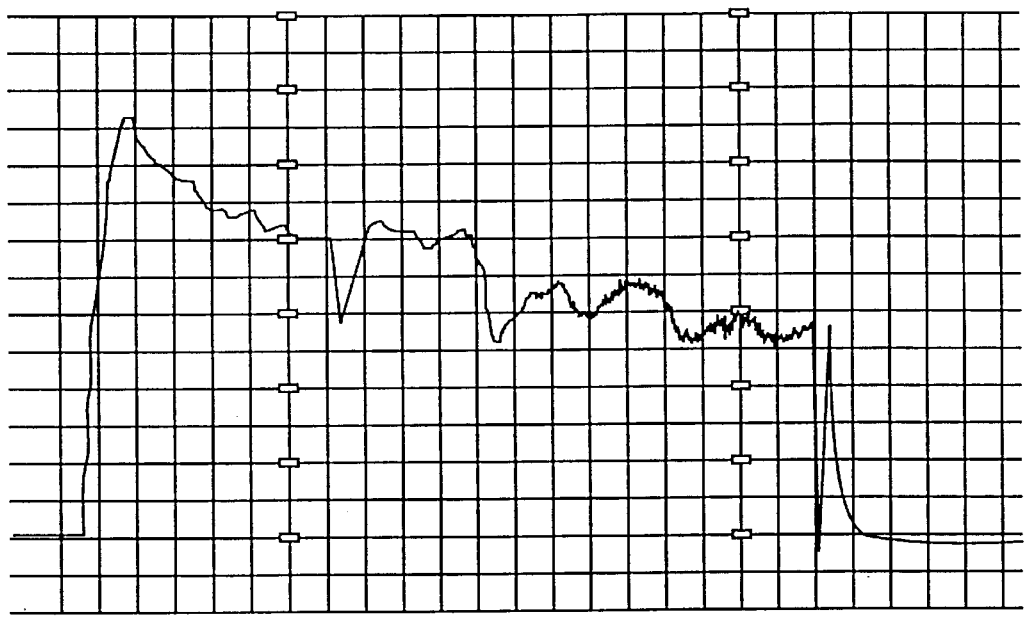
FIG. 6A, FIG. 6B, FIG. 6C and FIG. 6D. Myograph traces obtained using a mesenteric resistance artery.
Figure 6B:
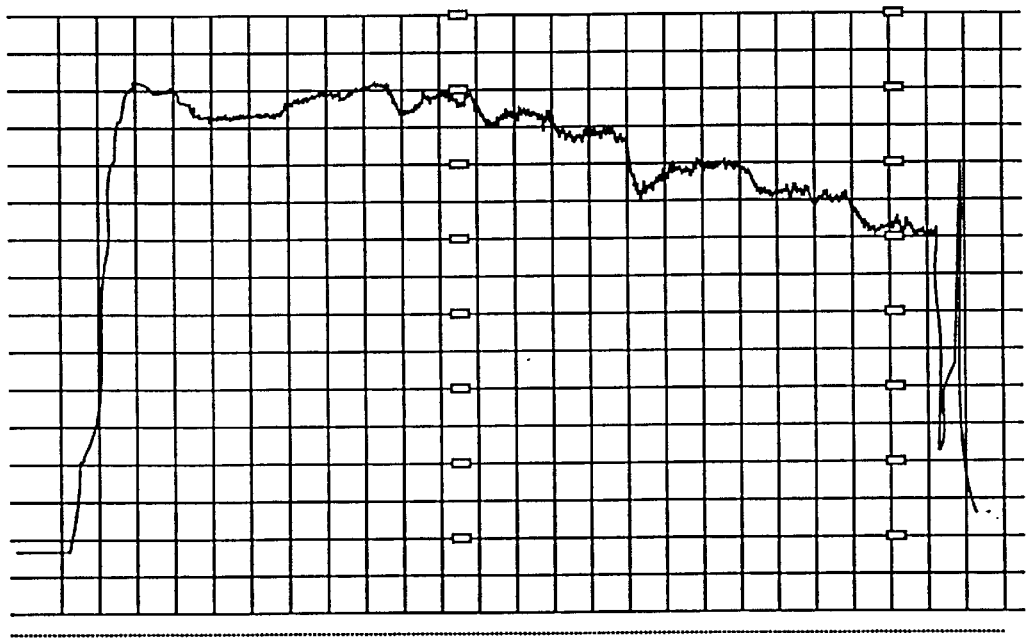
Figure 6C:
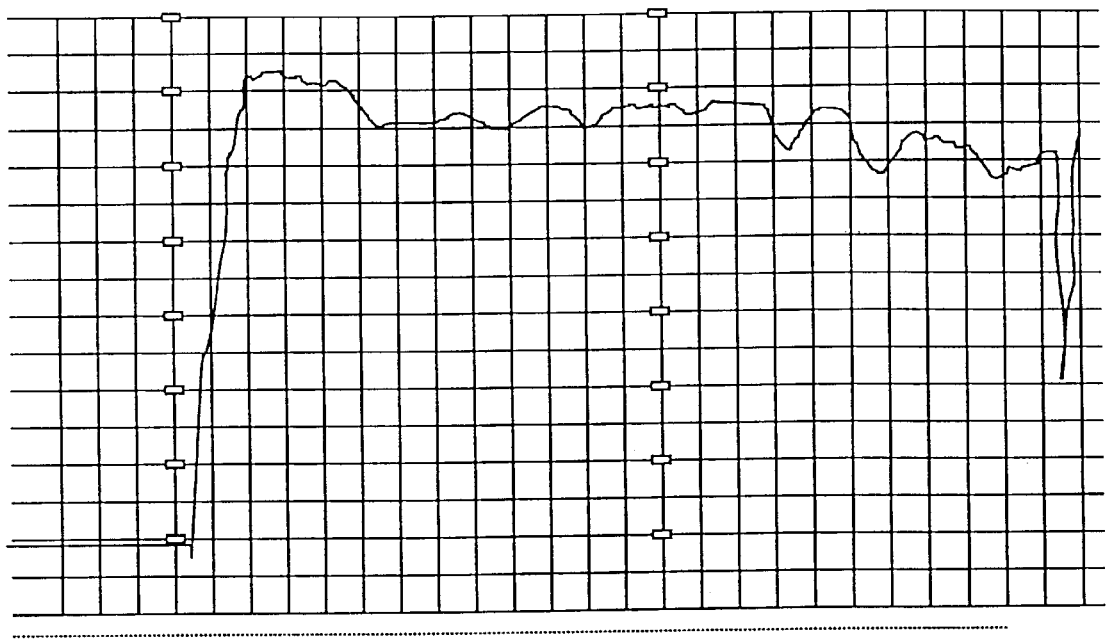
Figure 6D:
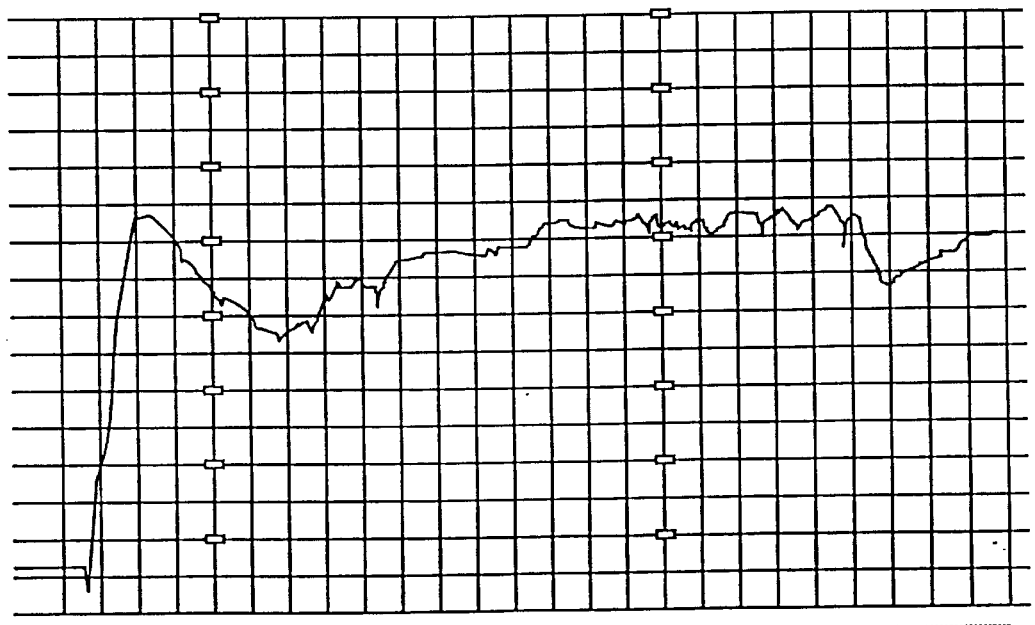

Since the results of the studies employing RTPCR, Western blot, and ICC were consistent with the hypothesis that $Ca^{2+}$-induced relaxation of resistance arteries is mediated by activation of a PvSN CaR additional studies were performed to determine whether denervation of the mesenteric resistance artery significantly inhibits $Ca^{2+}$-induced relaxation. Two approaches were developed. One approach entails acute denervation of the isolated arterial segment by direct application of a solution containing 0.75% phenol to the artery. This treatment completely blocks and often reverses $Ca^{2+}$-induced relaxation (FIG. 4A). The second approach consists of a sub-acute denervation in which a section of the proximal mesenteric bed is exposed via a midline incision and a 10% ethanolic solution of phenol is painted on the vessel (Bello-Reuss, et aL. 1975). The wound is closed and 72 hours allowed for degradation of the neural tissue. As with the acute preparation, the sub-acute treatment significantly inhibited the relaxation response to extracellular $Ca^{2+}$ (FIG. 4B). Together these data are consistent with the hypothesis that $Ca^{2+}$-induced relaxation is mediated by activation of the PvSN CaR.

The data demonstrate that physiologic concentrations of $Ca^{2+}$ induce relaxation of resistance arteries, that the perivascular nerve network expresses a $Ca^{2+}$ receptor that shares immunoreactivity with those described previously in the parathyroid and thyroid glands and in central nervous tissue, and are consistent with the hypothesis that activation of the PvSN CaR induces the release of a vasodilator transmitter.

In vessels that demonstrate a strong relaxation response to $Ca^{2+}$ (mesenteric resistance arteries nearly always relax to $Ca^{2+}$ and the larger vessels relax to variable degrees), NPS R467 induces a "biphasic" relaxation. By "biphasic" is meant that between 50–300 nM of the compound induces a relaxation which is of similar extent to the $Ca^{2+}$ relaxation, and at much higher concentrations 3–10 $\mu$M it causes a larger relaxation. The relaxation induced by the low range of the drug (10's of nM) is completely antagonized by 10 mM TEA which is a property of $Ca^{2+}$-induced relaxation. The relaxation induced by the higher concentration of the drug is not blocked by TEA (see FIG. 3B). The chemical structure of compound NPS R467 is shown below. NPS R467 is fully described in WO 95/11221, WO 93/04373, WO 94/18959, and WO 96/12697, all of which are incorporated herein.

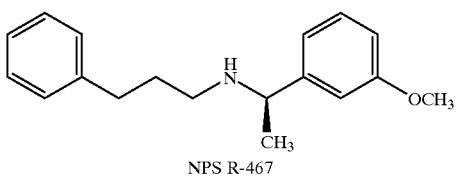

NPS R-467

In view of statements regarding the non-selective channel effects of this drug which occur at 4$\mu$M and above these data are consistent with the hypothesis that NPS R467, between 30–300 nM, activates the perivascular $Ca^{2+}$ receptor and induces relaxation; while at higher concentrations, it relaxes smooth muscle by a $Ca^{2+}$ channel inhibitory mechanism. The receptor that is present in the perivascular neuron is pharmacologically distinct from the receptor of the parathyroid since the perivascular receptor does not exhibit stereo-selectivity and on the basis of western blot data, consistently migrates at a lower molecular weight (120 kDa) compared with the parathyroid type.

Figure 18:
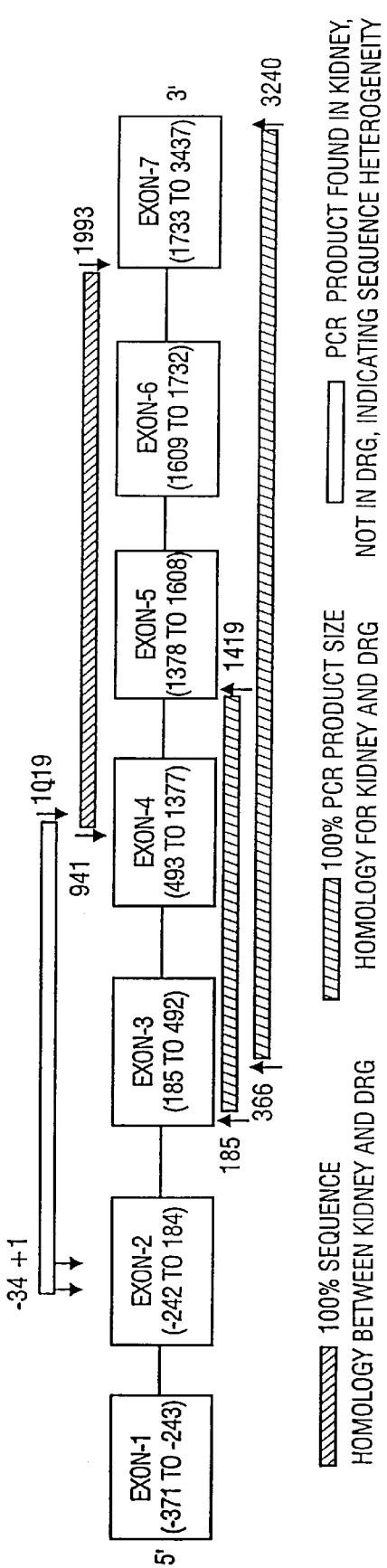
FIG. 18. The human parathyroid CaR gene consist of 7 exons; the transcriptional product is a 3808 bp mRNA with a 3437 bp open reading frame; the AUG start codon is located in exon 2. The structure of the rat CaR gene is similar to the human gene.

The full length cDNA encoding the parathyroid CaR is transcribed from a gene containing seven exons (FIG. 18). Exon 1 contains non-coding sequence, exon 2 contains both non-coding sequence and the transcription start site (+1), exons 3–7 contain the remainder of the 3' coding sequence. In preliminary studies it was found that there is 100% homology of the DRG sequence with the reported rat kidney sequence from nt 941 to nt 1993 spanning exons 4–7. In addition, primers designed to amplify message from the beginning of exon 3 (nt 185) to exon 5 (nt 1419) or to the 3' end (nt 3240) results in amplimers with identical molecular weights for both the DRG and the kidney. In contrast, when RTPCR™ is performed using a forward primer starting at the initiation codon (nt 1) or a codon 5' to this site (nt-35) and a reverse primer in exon 4 (nt 1091), the predicted size product in the kidney was obtained but not in the DRG. Amplification of DNA resulted in a predicted 956 bp product from kidney RNA, which is the positive control, and DRG RNA but not from RNA isolated from aorta, superior mesenteric artery, or heart. These findings indicate that there may be significant heterogeneity of the sensory nerve CaR possibly in exon 2. Heterogeneity at this site is significant because functional mutations of the CaR have been identified in this exon (Pollak et al., 1993).

Methodology

Chronic Sensory Denervation.

Pregnant rats are received at 15 days gestation and pups are delivered in a vivarium. On the first and second days of life, each pup is lightly anesthetized with halothane and given s.c. injection of capsaicin (50 mg/kg) or vehicle. The rats are then kept until 7–9 weeks of age at which time they are euthanized and tissue isolated. Sub-acute regional nerve destruction is performed. Eight week old rats are anesthetized, and a portion of the mesenteric trunk is exposed through a mid-line abdominal incision and painted with a 10% ethanolic solution of phenol or vehicle. The would is closed and the rats are allowed to recover for three days following which branches leading from the treated vessel segments are harvested for study. For each procedure, two methods are used to verify denervation of the arteries. One is a functional assay in which arteries isolated from sham or denervated rats are electrically stimulated under conditions that selectively activate perivascular sensory dilator nerves; the second is an immunocytochemical approach.

To demonstrate induction of chronic denervation, pups were treated with capsaicin as described above. At 8 weeks of age the rats were killed and whole mount preparations of mesenteric resistance arteries were prepared, stained with polyclonal anti-calcitonin gene related peptide (CGRP), which is the primary sensory nerve transmitter, and quantified using stereomorphologic methods (Schmidt-Schoenbein et al., 1977). The results showed that chronic denervation caused a 40% reduction in CGRP nerve fiber density, demonstrating this model.

Isolation and Preparation of Mesenteric Resistance Arteries.

Branch I and II mesenteric resistance arteries, internal diameter 175–225 mm, are isolated from the mesenteric arcade of male Wistar rats and placed in ice cold physiologic salt solution (PSS) of the following composition in mM: NaCl, 130–140; KCl, 4.7; $MgSO_4 \cdot 7H_2O$, 1.17; $NaHCO_3$, 5–15; $KH_2PO_4$, 1.15 and $Na_2HPO_4$, 1.10, $CaCl_2$, 1.0; HEPES, 50; and glucose, 5, with a pH of 7.4 when gassed with 95% air, 5% $CO_2$.

After cleaning of fat and connective tissue, the arterial segments are denuded of endothelium by rubbing a human hair in and out of the lumen. The vessel segments are then mounted between a force transducer and translation stage of a wire myograph using tungsten wire and the PSS is warmed to 37° C. and gassed with 95% air, 5% $CO_2$ to provide a pH of 7.4. The vessel segments are then stretched to a length which is equivalent to an internal diameter of 200–225 mm and allowed to equilibrate for 30 minutes. The vessels are then exposed to 5 mM norepinephrine for three 5 minute periods to induce reproducible contractile responses. The success of the endothelial denudation is verified by the absence of a relaxation response to acetylcholine. The relaxation response of the vessel to extracellular $Ca^{2+}$ is then determined to ensure that the perivascular sensory nerve network is intact by precontracting the artery with 5 mM norepinephrine then cumulative increasing extracellular $Ca^{2+}$ by the direct addition of $CaCl_2$ dissolved in 100 mM HEPES, pH 7.4. The vessel is then washed and allow to relax to baseline.

To determine whether the test compound is a vasodilator, the vessel is again precontracted by the addition of 5 mM norepinephrine, and after the force response reaches a steady state, the test compound is cumulatively added and the effect on force generation is determined. If the compound has vasodilator activity, two additional tests are carried out to establish whether the effect is specific for the sensory nerve $Ca^{2+}$ receptor. In the first test, the assay is repeated by adding the compound to arteries that have been pretreated with 5 mM quinacrine which is a phospholipase A2 antagonist that blocks $Ca^{2+}$ receptor mediated relaxation. In the second test, the ability of the compound to relax norepinephrine precontracted arteries, which have been isolated from rats that underwent chronic sensory denervation by neonatal treatment with capsaicin, is assessed. $Ca^{2+}$ receptor agonists that are found to be endothelium-independent vasodilators and whose dilator activity is blocked by quinacrine and sensory denervation are moved onto the tertiary in vivo blood pressure screen.

Measurement of CaR Expression.

The effect of sensory denervation on perivascular nerve CaR expression is assessed using western blot analysis. Total protein is extracted, size separated using 8% SDS-PAGE and transferred to nitrocellulose membrane for western blot analysis. The membranes are then stained with monoclonal anti-parathyroid CaR (1:7500) and anti-smooth muscle α-actin, then visualized using the enhanced chemiluminescence, and quantified using laser densitometry. The relative expression of CaR in each sample is then assessed as the ratio of the density of CaR staining; α-actin staining. Measurement of $Ca^{2+}$-induced relaxation.

Mesenteric resistance artery segments are isolated from sham treated and denervated rats and prepared for measurement of isometric force generation using the wire myograph system. After setting the vessels to a length which is equivalent to an inner diameter of 225 µm, and establishing reproducible responses to norepinephrine, they are precontracted with norepinephrine and the response to cumulative addition of extracellular $Ca^{2+}$ (1.5, 2.0 3.0, and 5.0 mM) is assessed. For each vessel, the maximal level of relaxation is recorded and used for comparisons. At the end of the protocol, the ability of the vessel to relax in response to addition of sodium nitroprusside (SNP) is assessed to determine the ability to relax in response to a non-neural stimulus.

Statistical Analysis.

The effect of chronic sensory and sub-chronic phenolic denervation on the magnitude of $Ca^{2+}$-induced relaxation and level of CaR expression is separately assessed and a correlation analysis is performed to determine the degree of linkage of $Ca^{2+}$-induced relaxation with CaR expression.

DNA Amplification.

Amplification of the perivascular sensory nerve CaR upstream of the exon 3 splice site of the CaR gene is performed using the 5' RACE PCR™ (Frohman et aL, 1988). Briefly, polyA mRNA from rat DRG and rat kidney is reverse transcribed to produce double stranded cDNA and specific adapters is ligated to the cDNA ends. The polymerase chain reaction is used to amplify CaR cDNA sequences between the 5' adapter encoded primer and the 3' (minus strand) primer complementary to nt-423 to nt-448 in exon 3 or rat kidney CaR gene. The resultant products is digested and subcloned into pBluescript for nucleotide sequence analysis.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Low, Physiologic Concentrations of Extracellular $Ca^{2+}$ Relax Isolated Arteries In an initial series of experiments the isometric force response of mesenteric resistance arteries of SHR and WKY was assessed to cumulative addition of norepinephrine in the presence of 1.25, 1.5 and 2.5 mmol/L extracellular $Ca^{2+}$ (Li, J., et al., 1993). In vessels of both strains the response to low dose norepinephrine was significantly depressed in the presence of 1.5 and 2.5 mmol/L $Ca^{2+}$ compared with 1.25 mmol/L $Ca^{2+}$, indicating that within a physiologic concentration range, extracellular $Ca^{2+}$ depresses the resistance artery force response.

In the course of studies designed to examine the hypothesis that the $Ca^{2+}$ force relationship of resistance arteries is altered in genetically hypertensive rats, it was discovered that physiologic concentrations of extracellular $Ca^{2+}$ affected the repeated contraction elicited by norepinephrine in $Ca^{2+}$-free medium. $Ca^{2+}$ was then incrementally increased in the presence of agonist while intracellular $Ca^{2+}$ and stress generation were simultaneously measured. $Ca^{2+}$ between 0.01 and 0.8 mmol/L caused an increase in force whereas raising $Ca^{2+}$ from 0.8 to 1.6 or from 1.6 to 2.5 mmol/L caused relaxation (FIG. 1).

Figure 2:
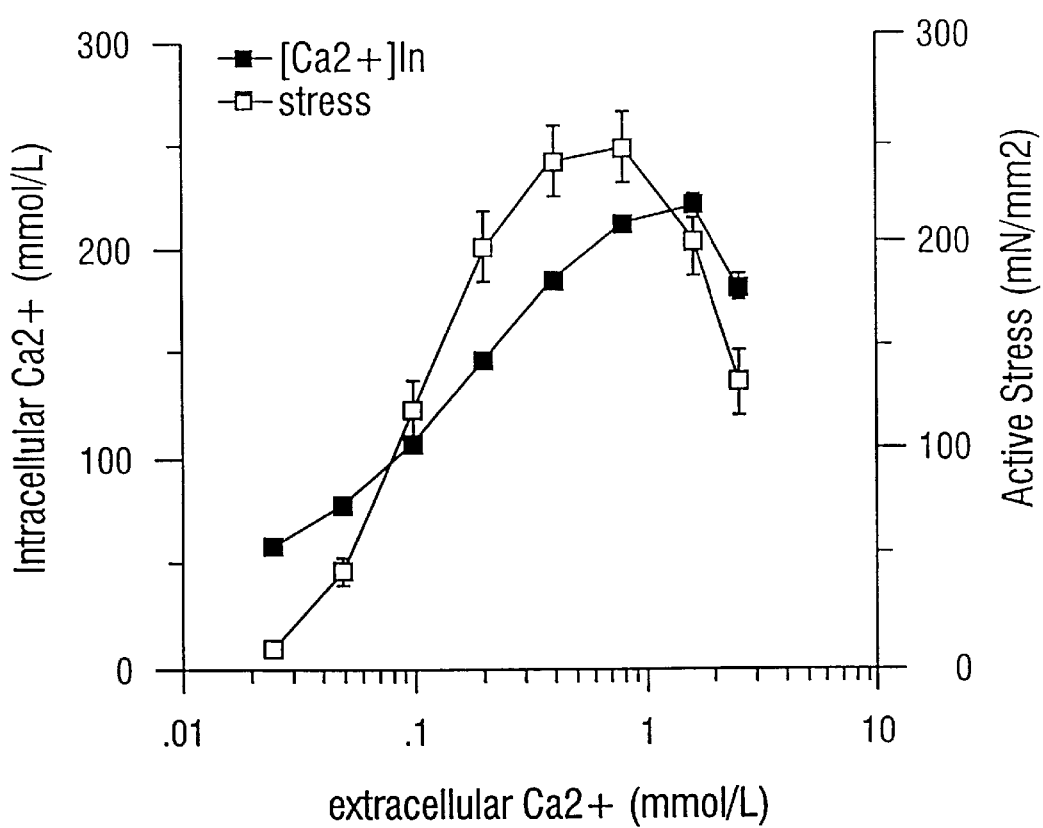
FIG. 2. Steady state force and $Ca^{2+}_{in}$ response determined as shown in FIG. 1. Increasing $Ca^{2+}_{out}$ from 0.8 to 1.6 decreased steady state force but not steady state $Ca^{2+}_{in}$. The level of force per unit $Ca^{2+}$ was less than predicted from the $Ca^{2+}$-force relationship seen during addition of low doses of $Ca^{2+}_{out}$. These data indicate that the decrease in force induced by 1.6 and 2.5 mM $Ca^{2+}$ is associated with decreased myofilament $Ca^{2+}$ sensitivity (Bian et al., 1 995b).

Mesenteric resistance arteries were isolated from Wistar rats; and intracellular $Ca^{2+}$ and isometric force were measured using a fura-based method and w ire myography (Bian, et aL, 1995b). Vessels were depleted of releasable $Ca^{2+}$ by repeated contraction with norepinephrine; and extracellular $Ca^{2+}$ was then cumulatively added back from 0.025-2.5 mmol/L in the presence of a n agonist. During contraction induced by norepinephrine, serotonin, and $PGF_{2\alpha}$, but not $K^+$, raising extracellular $Ca^{2+}$ from 0.8 to 1.6 and 1.6 to 2.5 mmol/L decreased active stress (FIG. 2). Although there was a transient decrease in intracellular $Ca^{2+}$ in response to both 1.6 and 2.5 mmol/L $Ca^{2+}$ steady state intracellular $Ca^{2+}$ only decreased significantly in response to 2.5 mmol/L extracellular $Ca^{2+}$ indicating that there was a decrease in myofilament $Ca^{2+}$ sensitivity (FIG. 2). The decrease in active stress induced by 1.6 and 2.5 mmol/L extracellular $Ca^{2+}$ was inhibited by blockade of $Ca^{2+}$-activated $K^+$ channels with charybdotoxin whereas inhibition of cyclooxygenase, protein kinase C, or the sarcoplasmic reticular $Ca^{2+}$-ATPase had no significant effect. It was concluded that extracellular $Ca^{2+}$ limits force generation by depressing myofilament $Ca^{2+}$ sensitivity and decreasing intracellular $Ca^{2+}$ secondary to activation of a $Ca^{2+}$-sensitive $K^+$ channel.

Figure 3A:
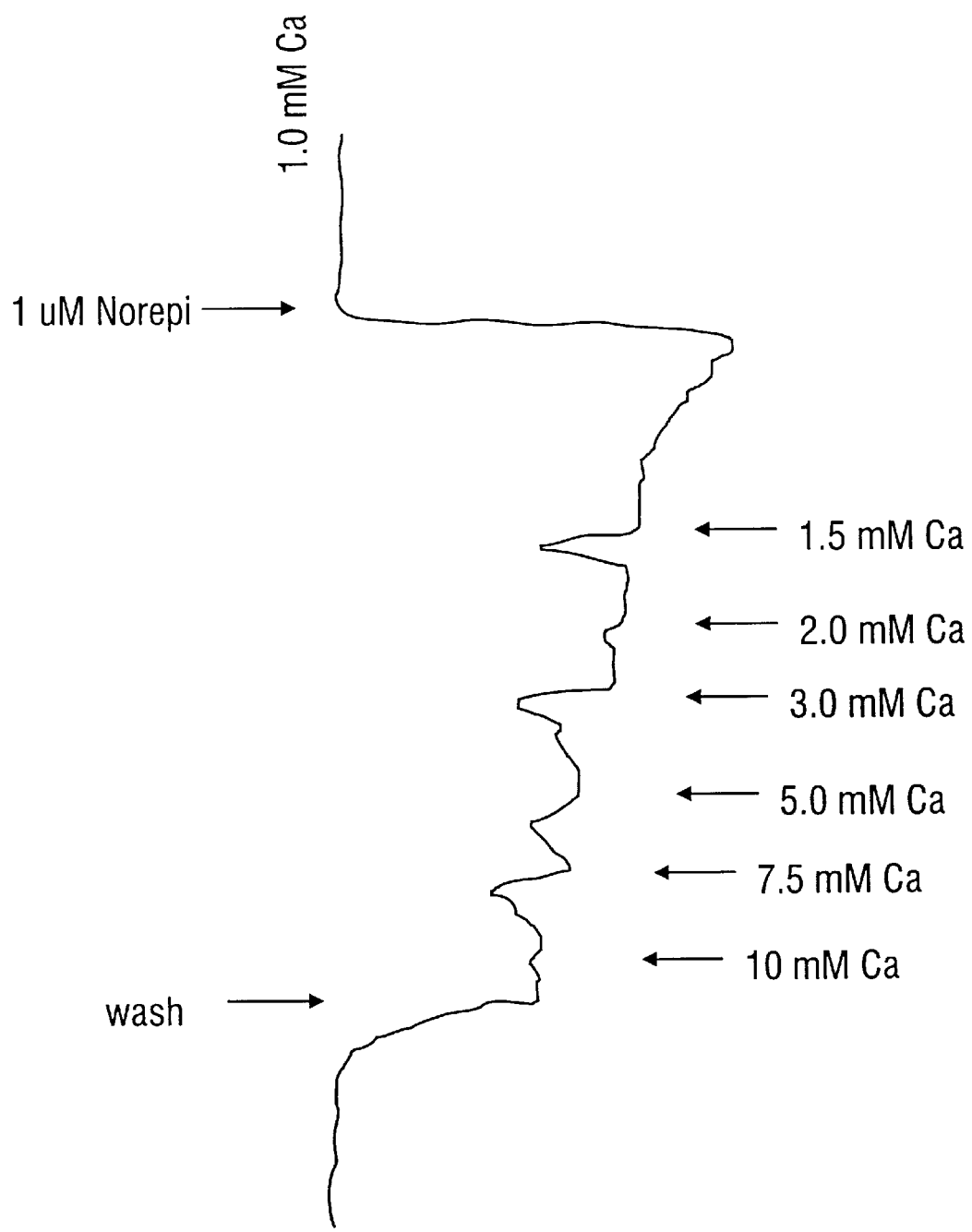
FIG. 3A. Isometric force response of mesenteric resistance arteries to increasing $Ca^{2+}_{out}$ from 1.0 to 1.5, 2, 3, 5, 7.5, and 10 nM (the vessel was never exposed to $Ca^{2+}$-free PSS).
Figure 3B:
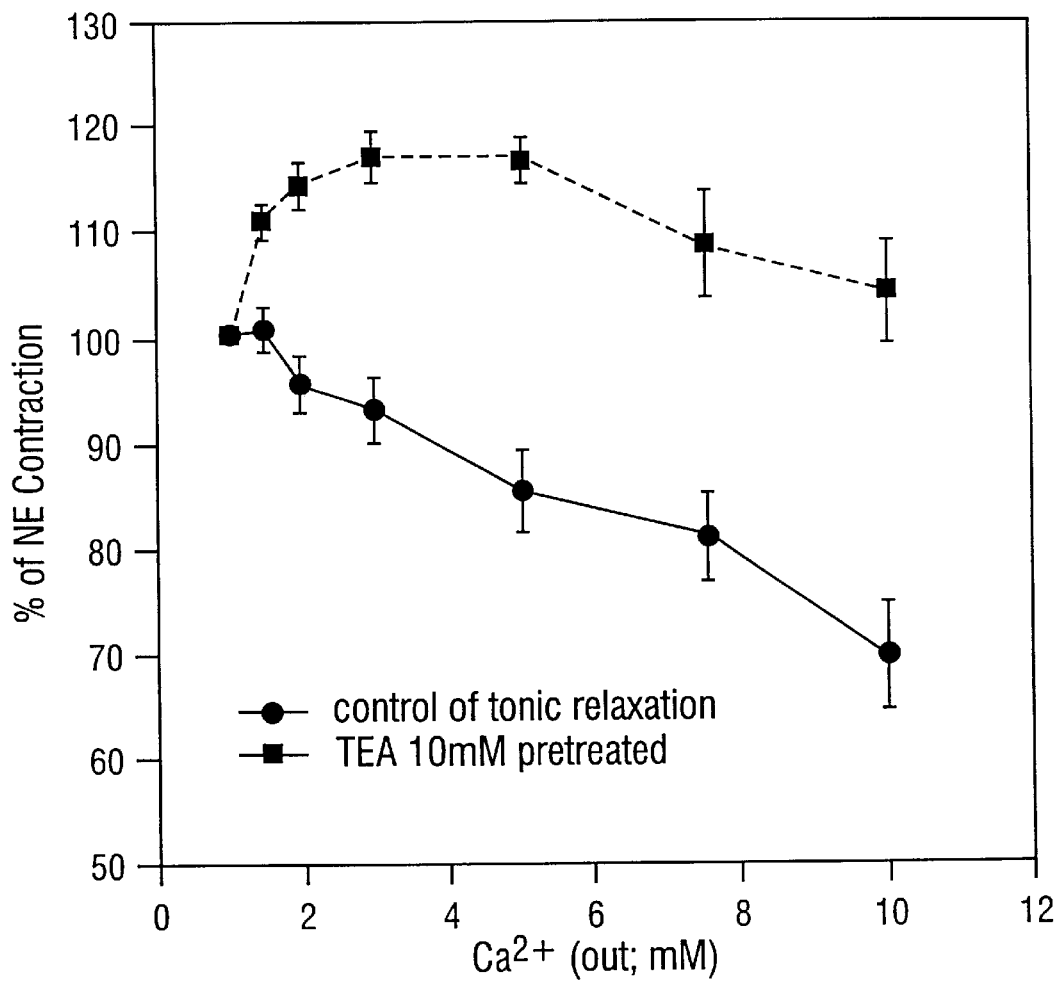
FIG. 3B. Inhibitory effect of pre-treatment with 10 mM TEA on the tonic component of the relaxation response to $Ca^{2+}_{out}$. The effect of TEA is significant at p<0.05; n=5.

While these data indicated that physiologic concentrations of $Ca^{2+}$ induce relaxation, there was the possibility that the $Ca^{2+}$ depletion step altered $Ca^{2+}$ handling by the cell membrane, thus, the inventors set out to determine whether similar results could be obtained without prior depletion of $Ca^{2+}$ and developed the protocol illustrated in FIG. 3. Mesenteric resistance arteries a re pre-contracted in low bicarbonate PSS containing 1 mmol/L $Ca^{2+}$ and 40 mmol/L HEPES at pH 7.4. The low bicarbonate is used to prevent precipitation of $Ca^{2+}$; HEPES is added to increase buffering capacity of the media. Once a stable level of tension is achieved, $Ca^{2+}$ is incrementally added back at 1.5, 2, 3, 5, 7.5 and 10 mmol/L. As with earlier results a biphasic relaxation response characterized by a transient (phasic) relaxation which leveled off at a steady state "tonic" level that was level with or lower than the preceding baseline was observed (FIG. 3A). Consistent with prior results obtained using charybdotoxin, the relaxation was completely inhibited by $K^+$ channel blockade by pre-treatment with 10 mmol/L TEA (FIG. 3B). Evidence that $Ca^{2+}$-induced relaxation is partially inhibited by removal of the endothelium and by pre-treatment with L-NAME indicating a role for endothelium and NO was also found.

From the results of FIGS. 1–3 it was concluded that that physiologic concentrations of $Ca^{2+}$ relax resistance arteries and that the relaxation is associated with a decrease in myofilament $Ca^{2+}$ sensitivity. Both of these properties are consistent with the hypothesis that $Ca^{2+}$-induced relaxation is associated with cell membrane receptor-linked process.

EXAMPLE 2

Demonstration of the PvSN CaR

During the performance of the above studies, the first report of the cloning and molecular characterization of the membrane spanning $Ca^{2+}$ receptor appeared (Brown, et al., 1993a; 1995) which suggested the possibility that this, or a similar receptor is present on the vascular smooth muscle cell and mediates $Ca^{2+}$ induced relaxation. After a report describing the cloning of the $Ca^{2+}$ receptor from rat kidney appeared (Riccardi, et al. 1995), intron spanning PCR™ primers were designed to generate a 1045 bp amplimer from the rat kidney CaR cDNA. Consistent with prior reports, a message encoding the CaR was found in kidney (used as a positive control) but not in aorta, superior mesenteric artery, or mesenteric resistance artery (FIG. 4A). On the basis of later reports that the $Ca^{2+}$ receptor is expressed in neuronal tissue (Ruat, et al. 1995), the inventors realized that it was possible for $Ca^{2+}$ receptor protein to be expressed in the perivascular nerve network, and for its message to go undetected since it would be restricted to cell bodies located proximal to the perivascular nerve processes, i.e. in the dorsal root ganglia (DRG). Subsequent studies verified that the DRG expresses message encoding the CaR (FIG. 4B).

The inventors next sought to verify the molecular results using CaR specific antibody. The antibody was successfully used in immunocytochemical and western blot analyses to verify that CaR is present in the vascular wall and expressed in perivascular nerves.

Western blot analysis:

Mesenteric resistance arteries and thyroparathyroid gland were isolated from Wistar rats and homogenized as described previously (Ishibashi, et al. 1995). Protein was then size separated on 8% SDS-PAGE and electroblotted onto nitrocellulose membrane for western blot analysis. The membrane was then incubated with monoclonal anti-CaR (ADD) and the protein-antibody complex was visualized using the enhanced chemiluminescence method (ECL Amersham). Protein bands with a molecular weight in the range of 120–170 kDa which co-migrate with CaR in the thyroparathyroid extract are present in the mesenteric resistance artery. These data were interpreted to indicate that CaR protein is present in the mesenteric resistance artery (Brown, et al., 1993a; 1995).

The ICC was used to examine the hypothesis that a CaR is expressed in the perivascular nerve network of the mesenteric resistance artery. Mesenteric resistance arteries were perfused with saline to remove blood, then placed on gelatin coated slides and fixed for 10 minutes in ice cold methanol, then stained with anti-CaR (ADD) with the biotin-avidin HRP system (Vector Labs). The results indicated that a nerve-like network that stains positively for CaR is present in the adventitia.

EXAMPLE 3

Effect of CaR Agonists on Resistance Arteries

Rank-order Potency of Parathyroid CaR Agonists on the Perivascular CaR.

The rank order potency of 10 compounds supplied by NPS as vasorelaxants of norepinephrine precontracted mesenteric resistance arteries was studied. Two of the compounds were commercially available $Ca^{2+}$ channel antagonists, two were polyamine-type CaR agonists, the others were structural analogs of NPS R467. All of the compounds except the polyamines relaxed norepinephrine precontracted resistance arteries. The rank order potency of the structural analogs of NPS R467 as vasorelaxants was different from their previously established rank order as parathyroid CaR agonists (Table 1). One interpretation of this differential potency is that the perivascular CaR is pharmacologically different from the parathyroid CaR and results of molecular studies described in Project 6 support this concept.

TABLE 2

| Preparation | 1 | 2 | 3 | 4 | 5 | 6 | 7 | 8 | 9 | 10 |
|---|---|---|---|---|---|---|---|---|---|---|
| parathyroid | C | D | H | G | F | E | I | A | J | B |
|  | 11 nM | 72 nM | 0.3 µM | 0.7 µM | 1.7 µM | 2.9 µM | 15 µM | 21 µM | 50 µM | 0.5 mM |
| vascular | J | H | G | E | I | C | F | D | A | B |
|  | 0.2 µM | 0.5 µM | 0.9 µM | 1.3 µM | 0.2 µM | 2.4 µM | 4.9 µM | 14 µM | na | na |

Results of Rank Order Potency Study

Note: I and J are $Ca^{2+}$ channel antagonists, A and B are polyamines, na = no activity, others are analogs of NPS R467. H = NPS R831.
The structure of compound D is shown below.

TABLE 2-continued

Results of Rank Order Potency Study

| Preparation | 1 | 2 | 3 | 4 | 5 | 6 | 7 | 8 | 9 | 10 |
|---|---|---|---|---|---|---|---|---|---|---|

Compound A

Compound B

Compound D

Compound H

Compound I

Compound G

Of interest, these studies demonstrated that NPS R831 relaxes precontracted arteries with the same potency as it activates the parathyroid CaR system (Table 1). On this basis NPS R831 was chosen for further study, both in terms of mechanisms of actions, and for possible blood pressure lowering effects. The chemical structure of NPS R831 is shown below.

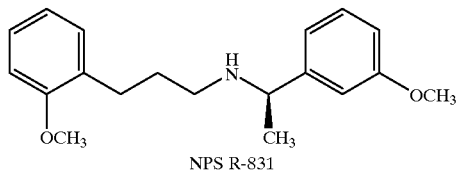

NPS R-831

Comparison of the Effect of NPS 831 on Resistance Arteries Precontracted with Either Depolarizing K$^±$ or Norepinephrine.

Prior studies have shown that the parathyroid CaR agonists of the NPS R467 class block voltage sensitive Ca$^{2+}$ channel at mid-micromolar concentrations. Additional studies to determine whether the parathyroid Ca$^{2+}$ receptor agonist NPS H831 relaxes isolated arteries by stimulating the perivascular CaR or by an non-specific effect to block voltage sensitive Ca$^{2+}$ channels present on smooth muscle were conducted. The rationale was based on the facts that (a) K$^+$-induced contraction is the result of influx of Ca$^{2+}$ into the cell through voltage gated Ca$^{2+}$ channels, and (b) Ca$^{2+}$-induced relaxation is not observed during K$^+$ depolarization. Thus, CaR agonist mediated relaxation observed during K$^+$ induced contraction would reflect Ca$^{2+}$ channel blocking activity while relaxation observed during K$^+$-induced contraction would reflect Ca$^{2+}$ channel blocking activity while relaxation observed during norepinephrine-induced contraction (which results from both Ca$^{2+}$ release and Ca$^{2+}$ entry) would be a mixture of Ca$^{2+}$ receptor stimulated relaxation and Ca$^{2+}$ channel activity.

Figure 11:
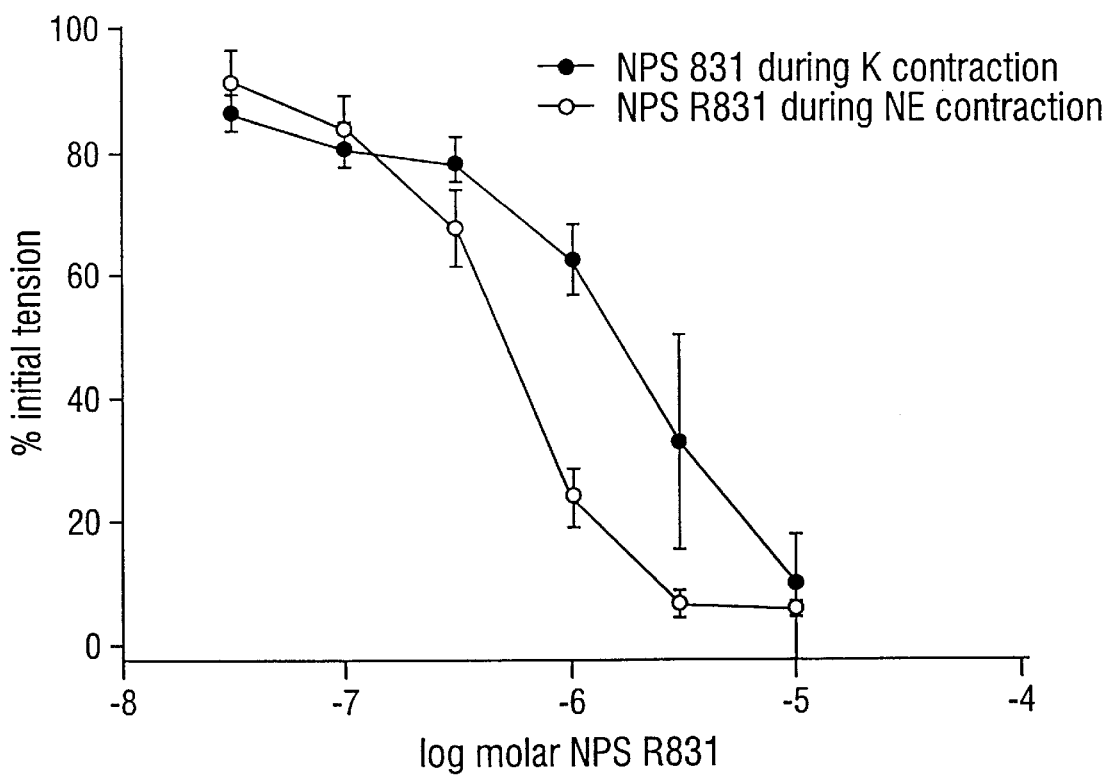
FIG. 11. Effect of NPS R831 on mesenteric arteries precontracted with either 5 $\mu$M norepinephrine or 100 mM $K^+$. Since relaxation occurring during $K^+$ depolarization reflects primarily $Ca^{2+}$ channel blocking activity, the results indicate that NPS R831 blocks $Ca^{2+}$ channels with an $IC_{50}$ of approximately 1.5 $\mu$M and is consistent with the hypothesis that the higher sensitivity to NPS R831 observed during precontraction with norepinephrine reflects activity on the perivascular CaR.

Mesenteric resistance arteries were precontracted with either 100 mM K$^+$ (in the presence of 1 $\mu$M phentolamine) or 5 $\mu$M norepinephrine and response to cumulative addition of NPS R831 (10 nM to 50 $\mu$M) determined. The relaxation response to NPS R831 was significantly shifted to the right (less sensitive) during K$^+$-induced contraction compared with norepinephrine-induced contraction, indicating that two mechanisms are operant, i.e., a Ca$^{2+}$ channel blocking mechanism of action at mid-$\mu$M concentrations and a second, possibly perivascular CaR mediated component at sub-micromolar concentrations (FIG. 11). To determine that the high sensitivity component observed during norepinephrine-induced contraction is mediated by the perivascular CaR two additional studies are conducted.

The goals of these studies are (1) to determine whether the shift in the response to NPS R831 during K$^+$ vs norepinephrine-induced contraction is also observed with the S-enantiomer of the compound which should be significantly less active in the norepinephrine contracted preparation that the R-enantiomer; and (2) to determine whether the high-sensitivity component of the relaxation induced NPS R831 can be blocked by acute phenolic denervation of the artery. The rationale for these studies is the observation that acute phenolic denervation ablates/attenuates Ca$^{2+}$-induced relaxation by destroying perivascular nerves and thus would block the NPS R831 effect if it were mediated by activation of the perivascular CaR.

EXAMPLE 4

Figure 12:
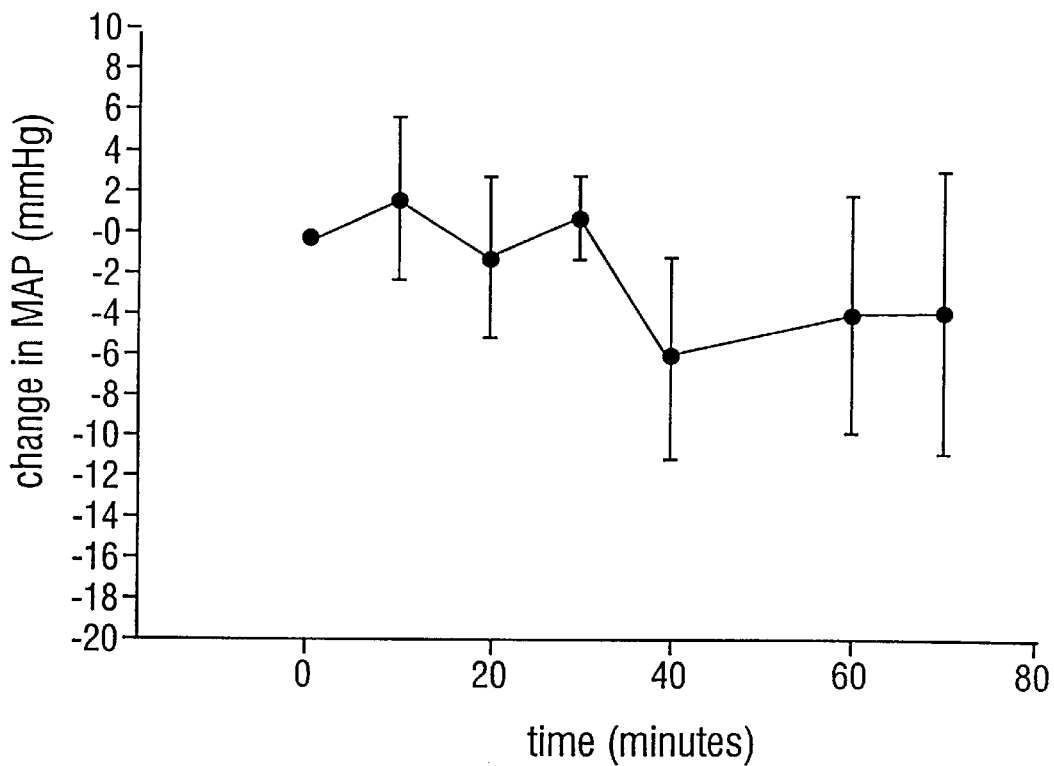
FIG. 12. Effect of bolus administration of 3 $\mu$mol/kg NPS R467 on mean arterial pressure (carotid artery catheter) of conscious SHR rats.

Effects of Parathyroid Ca$^{2+}$ Receptor Agonists on Blood Pressure in Spontaneously Hypertensive and Normotensive Rats The initial studies assessed the effect of bolus administration of NPS R467 on mean arterial pressure of conscious rats of both strains. In agreement with prior findings, NPS 467 had a modest and slowly developing (over 30–40 min) blood pressure lowering effect in both strains (FIG. 12).

Figure 13:
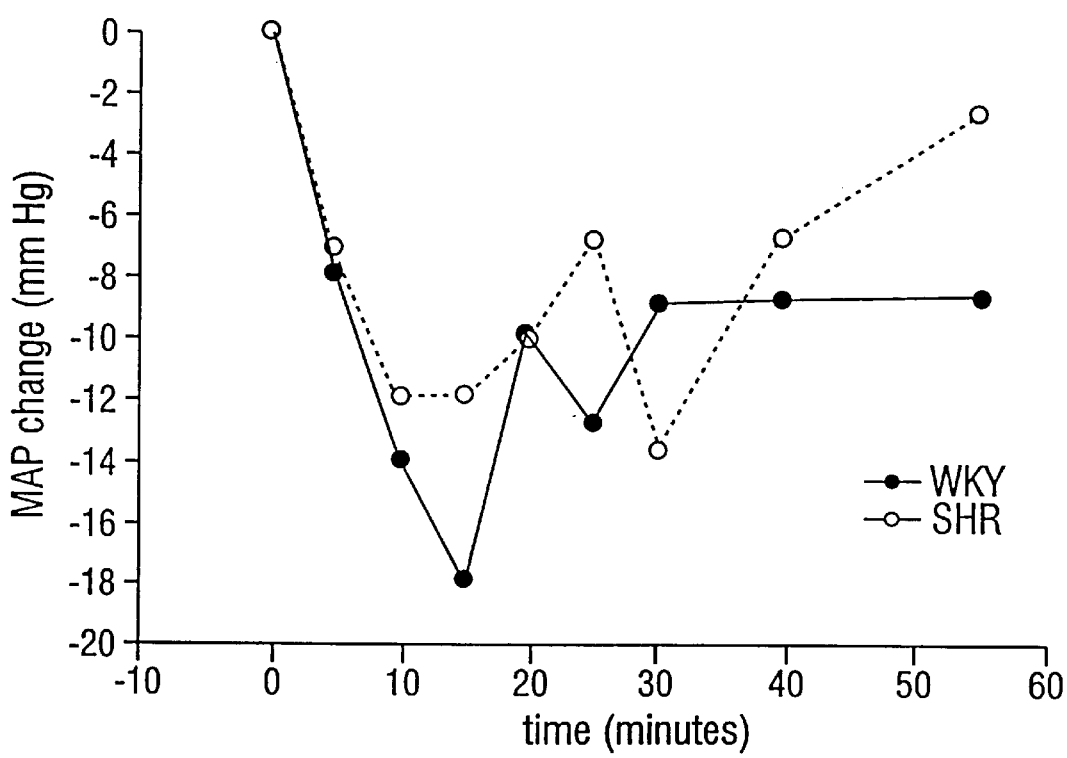
FIG. 13. Effect of bolus administration of 1 $\mu$mol/kg NPS R831 on mean arterial pressure (carotid artery catheter) of conscious SHR and WKY.

As noted, one result of the studies in Example 1 was the identification of NPS R831 as a candidate compound for assessment of blood pressure lowering effects. A study was performed in which the effect of a bolus injection of NPS R831 on blood pressure of a single SHR and a single WKY rat were measured. The results were very promising in that NPS R831 had a moderately rapid (within 5 min) blood pressure lowering effect in both strains (FIG. 13).

EXAMPLE 5

Effect of Chronic Capsaicin-induced Denervation on CaR Receptor Expression and Ca$^{2+}$-induced Relaxation This goal of this study was to test the hypothesis that chronic capsaicin-induced sensory denervation of the rat proportionately reduces perivascular nerve CaR expression and Ca$^{2+}$-induced relaxation of isolated arteries. The rationale of the study was that if Ca$^{2+}$ induces relaxation of isolated arteries by activating the perivascular CaR which in turn released a vasodilator substance, then reduction of perivascular sensory nerve content should decreased Ca$^{2+}$-induced relaxation.

Figure 14:
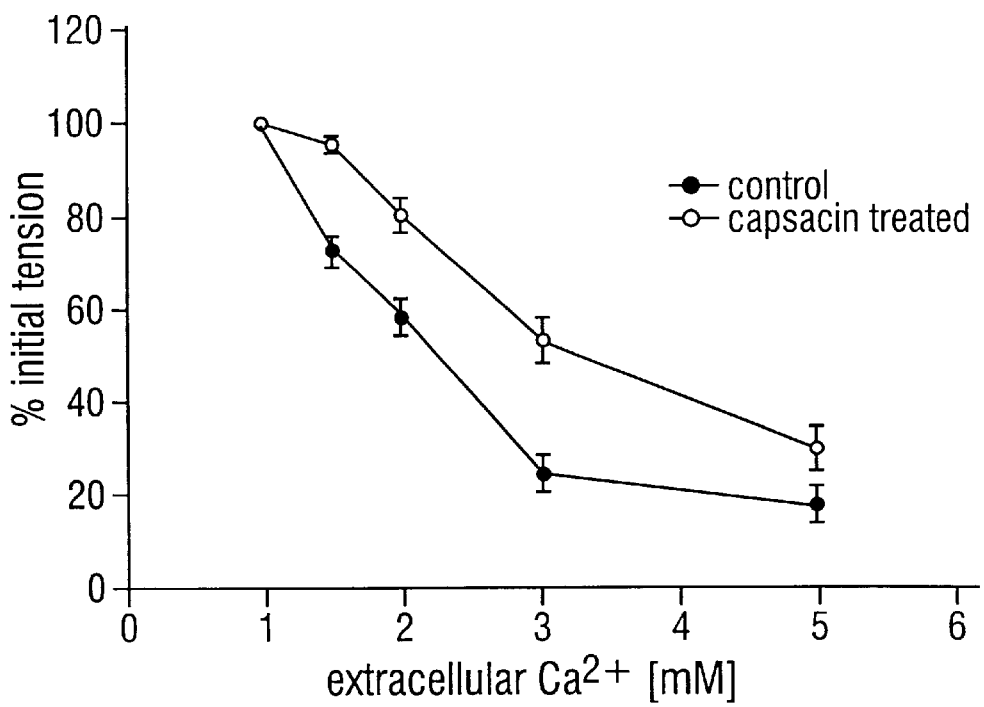
FIG. 14. $Ca^{2+}$-induced relaxation was significantly attenuated in vessels isolated from rats that underwent chronic capsaicin-induced sensory denervation, (p<0.001 for control vs. denervated, n=6–7). + indicates a significant effect of denervation at p<0.05.
Figure 15:
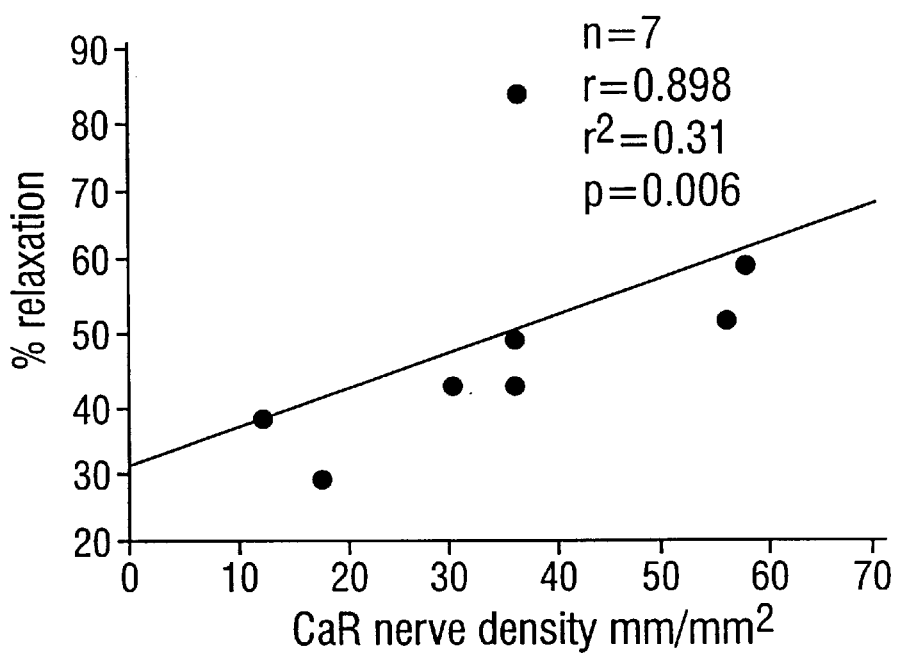
FIG. 15. Relationship between CaR density and relaxation induced by 3 mM $Ca^{2+}$ in the presence of 5 $\mu$M norepinephrine. The magnitude of $Ca^{2+}$-induced relaxation was positively correlated with the CaR content of the mesenteric perivascular nerve network.

The capsaicin model has been established and the results of several groups of animals show that capsaicin denervation significantly decreases staining for CGRP and the perivascular CaR (using KK3 antiserum) and attenuates Ca$^{2+}$-induced relaxation (FIG. 14), such that there is a positive correlation between perivascular CaR density and extent of relaxation (FIG. 15). The results have been presented (Mupanomunda et al., 1997). Additional studies quantify the effect of capsaicin-induced denervation on CaR content using western blot analysis.

EXAMPLE 6

Pharmacologic Dissection of Vasodilator Substance (transmitter) Mediating Ca$^{2+}$-induced Relaxation Studies were performed to determine the chemical nature of the vasodilator substance that mediates Ca$^{2+}$-induced relaxation. Multiple antagonists were used to determine whether a vasodilator substance previously identified in sensory nerves is the mediator. The candidate substances and the pharmacologic approach for assessment are listed in Table 2. The results of this portion of the study showed that the vasodilator substance is not endothelium derived and is not nerve derived nitric oxide or related NADPH oxidase derived nitroso-thiol. Moreover, blockade of the common sensory nerve peptide transmitter dilators (CGRP, tachykinins, VIP) had no effect suggesting that the relaxation is not mediated by a common peptide transmitter.

TABLE 3

Antagonists Tested to Identify the Sensory Nerve Dilator

| Candidate substance | Antagonist(s) | Result |
| --- | --- | --- |
| EDRF | denudation | no effect |
| nitric oxide (NO) | L-NAME | no effect |
| carbon monoxide (CO) | tin protoporphorin IX | no effect |
| prostanoids | indomethacin | partial effect at 1.5 mM CA$^{2+}$ |
| CGRP | CGRP (8–37) | no effect |
| substance P | spantide II, SRI40333, CP99, 994 | no effect |
| neurokinin A | SR48968 | no effect |
| neurokinin B | SR 142801 | no effect |
| galanin | galantide | no effect |
| dynorphin | nor-binaltorphmine | no effect |
| VIP | 4 Cl-D-Phe$^6$,Leu$^{17}$-VIP | no effect |
| CRF | α-helical CRF | no effect |
| nitroso-thiols | tropine | no effect |

EDRF = endothelium derived relaxing factor; CGRP = calcitonin gene-related peptide, VIP = vasoactive intestinal peptide; CRF = corticotropin releasing factor On the basis of prior results which showed that Ca$^{2+}$-induced relaxation is antagonized by blockage of K channels with TEA and the K$_{Ca}$ channel antagonist charybdotoxin, and is not observed during contraction induced by depolarizing $K^+$, it was deduced that the nerve derived vasodilator substance was one of the cytochrome P450 derived hyperpolarizing factors that have recently been identified in endothelial cells and astrocytes.

Figure 16:
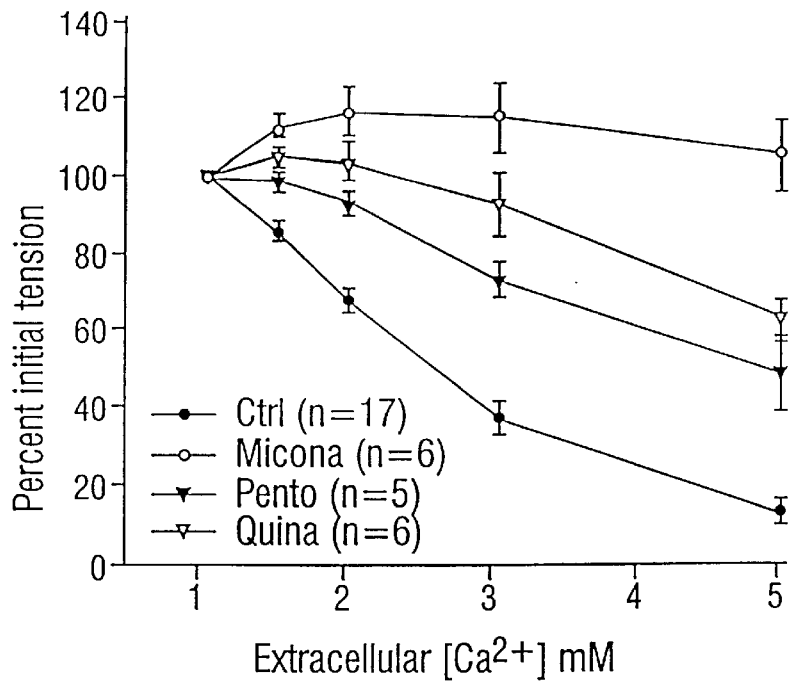
FIG. 16. $Ca^{2+}$-induced relaxation under control conditions and during blockade of cytochrome $P_{450}$ with 3 $\mu$M micoanzole or 1 $\mu$M pentobarbital or blockade of phospholipase $A_2$ with 1 $\mu$M quinacrine. All three agents significantly attenuated $Ca^{2+}$-induced relaxation atp<0.05.
Figure 17:
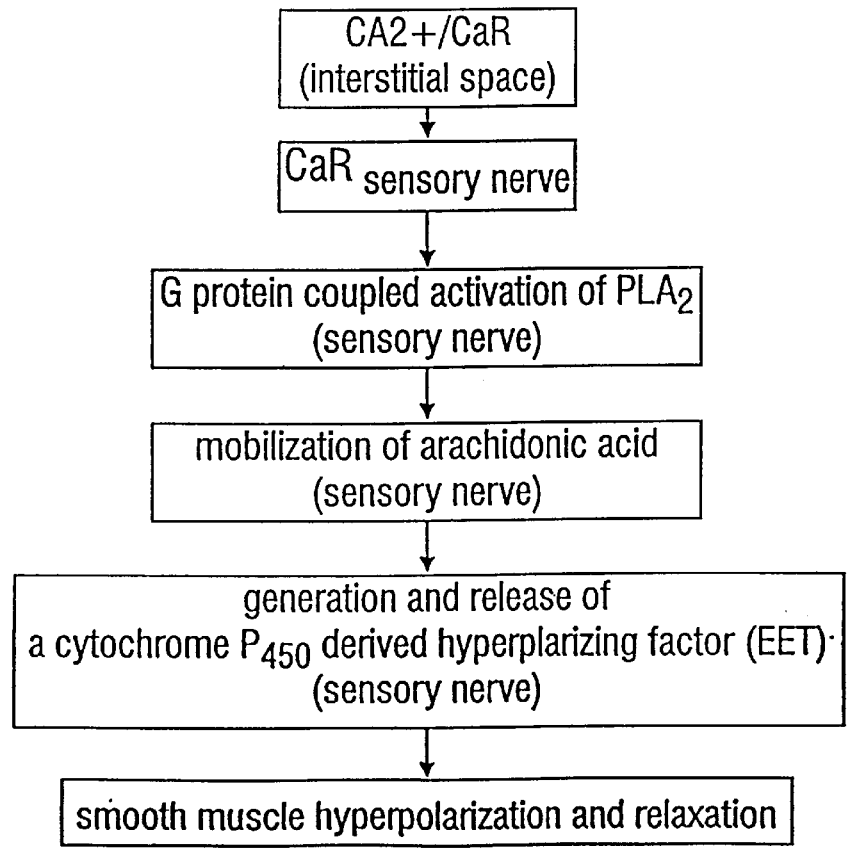
FIG. 17. Model of the pathway by which activation of the perivascular CaR by $Ca^{2+}$ or CaR agonist could induce arterial dilation.

To verify this deduction, the effect of two cytochrome P450 antagonists, pentobarbital and miconazole on $Ca^{2+}$-induced relaxation was assessed. Both of these compounds completely antagonized $Ca^{2+}$-induced relaxation at $Ca^{2+}$ ranging from 1.5–3 mM and significantly attenuated relaxation induced by 5 mM $Ca^{2+}$ (FIG. 16). Since it has been reported that arachodonic acid derived from phospholipase A2 serves as the biologic substrate for the cytochrome P450 enzyme, the effect of blockage of $PLA_2$ with quinicrtine on $Ca^{2+}$-induced relaxation was assessed and it was found that this compound significantly attenuates $Ca^{2+}$-induced relaxation (FIG. 16). These results have been incorporated into a mechanistic model (FIG. 17) for the mechanism by which $Ca^{2+}$ or CaR agonists relax blood vessels.

EXAMPLE 7

RTPCR™ analysis of CaR cDNA from Dorsal Root Ganglia (DRG)

A series of studies have been completed which indicate that a novel splice variant of the CaR may be present in the DRG. RTPCR™ analysis of the DRG CaR was performed and it was found that there is complete sequence homology between nt 941 and 1993 for the DRG cDNA and the published rat kidney sequence (FIG. 18). In addition, it was found that predicted mol wt amplimers are obtained for both the DRG and kidney when primers made to sequence in putative exon 3 (nt 185 to nt 1419 and nt 366 to nt 3240) are used. In contrast, when primers 5' to this region are used (nt 1 to 1019 and nt-34 to 1019), the predicted product is only obtained in the kidney. Rapid amplification of CDNA ends (RACE) using the marathon RACE kit was performed and an amplimer was obtained. These results suggest that there is significant heterogeneity in exon 2 of the DRG vs kidney CaR genes. This heterogeneity is verified by using standard cloning and sequence analysis.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

Those of skill in the art will find equivalents and obvious modifications to these procedures. The following references are incorporated by reference herein in pertinent part for the reasons cited in the text.

Aalkjaer, et al., "Evidence for increased media thickness, increased neuronal amine uptake, and depressed excitation-contraction coupling in isolated resistance vessels from essential hypertensives," *Circ. Res.*, 61:181–186, 1987.

Ackley, Barrett-Connor, Suarez, "Dairy products, calcium and blood pressure," *Am. J. Clin. Nutr.*, 38:457–461, 1983.

Anderson, Wilson, Odell, Kannel, "An updated coronary risk profile: a statement for health professionals," *Circulation*, 83:357–363, 1991.

Andriantsitohaina, et al., "Effect of neuropeptide Y on intracellular $Ca^{2+}$ and force development by isolated mesenteric resistance arteries," *J. Vascular Res.*, 30:309–314, 1993.

Arvola, Ruskoaho, Porsti, "Effects of high calcium diet on arterial smooth muscle function and electrolyte balance in mineralocorticoid-salt hypertensive rats," *Br. J. Pharmacol.*, 106:157–165, 1993.

Ayachi, "Increased dietary calcium lowers blood pressure in the spontaneously hypertensive rat," *Metabolism*, 28:1234–1238, 1979.

Belizan and Villar, "The relationship between calcium intake and edema-, proteinuria-and hypertension gestosis: An hypothesis," *Am. J. Clin. Nutr.*, 33:2202–2210, 1980.

Bello-Reuss, et al., "The effect of acute unilateral renal denervation in the rat," *J. Clin. Invest.* 56:208–217, 1975.

Bian and Bukoski, "Modulation of resistance artery force generation by extracellular $Ca^{2+}$," *Am. J. Physiol. (Heart Circ. Physiol.)*, 269:H230–H238, 1995b.

Bian and Bukoski, "Myofilament $Ca^{2+}$ sensitivity of normotensive and hypertensive resistance arteries," *Hypertension*, 25:110–116, 1995a.

Bian, Ishibashi, Bukoski, "Modulation of resistance artery force generation by extracellular $Ca^{2+}$," *Am. J. Physiol. (Heart Circ. Physiol.)*, 269:H230–H238, 1995.

Bohr, D. F., "Vascular smooth muscle: dual effect of calcium," *Science*, 19:597–599, 1963.

Brain, et al., "Calcitonin gene-related peptide is a potent vasodilator," *Nature* 313:54–56, 1985.

Brown, E. M., "Extracellular $Ca^{2+}$ sensing, regulation of parathyroid cell function, and role of $Ca^{2+}$, and other ions as extracellular (first) messengers," *Physiol. Rev.* 71:371–411, 1991.

Brown, et aL, "Calcium-ion-sensing cell-surface receptors," *N. Engl. J. Med.*, 333:234–240, 1995.

Brown, et al., "Cloning and characterization of an extracellular $Ca^{2+}$-sensing receptor from bovine parathyroid," *Nature*, 366:575–580, 1993a Brown, Gamba, Riccardi, Lombardi, Butters, Kifor, Sun, Hediger, Lytton, Hebert, "Cloning and characterization of an extracellular $Ca^{2+}$-sensing receptor from bovine parathyroid," *Nature*, 366:575–580, 1993b.

Bucher, Cook, Guyatt, Lang, Cook, Hatala, Hunt, "Effects of dietary calcium supplementation on blood pressure—a meta-analysis of randomized controlled trials," *J. Am. Med Assoc.*, 275(13):1016–1022, 1996b.

Bucher, Guyatt, Cook, Hatala, Cook, Lang, Hunt, "Effect of calcium supplementation on pregnancy-induced hypertension and preeclampsia—a meta-analysis of randomized controlled trials," *J. Am. Med Assoc.*, 275(14):1113–1117, 1996a.

Buchholz, et al., "Age-related changes in the sensitivity of sympathetic nerves to altered extracellular calcium in tail arteries of F-344 rats," *Neurobiol. Aging*, 15:197–201, 1994.

Bukoski and McCarron, "Altered aortic reactivity and lowered blood pressure associated with high $Ca^{2+}$ intake in the SHR," *Am. J. Physiol.*, 251:H976–983, 1986.

Bukoski, "Intracellular free $Ca^{2+}$ in mesenteric resistance arteries and primary cultured myocytes of the spontaneously hypertensive and normotensive rat," *J. Hypertension*, 8:37–43, 1990.

Bukoski, et al., "Effect of 1,25(OH)$_2$ vitamin D$_3$ and ionized Ca$^{2+}$ on $^{45}$Ca uptake by primary cultures of aortic myocytes of spontaneously hypertensive and Wistar-Kyoto normotensive rats," *Biochem. Biophys. Res. Comm.* 146:1330–1335, 1987.

Bukoski, et al., "Intracellular Ca$^{2+}$ and force determined simultaneously in isolated resistance arteries," *Am. J. Physiol. (Heart)* 257:H1728–1735, 1989.

Bukoski, et al., "Intracellular Ca$^{2+}$ and force generation determined in resistance arteries of normotensive and hypertensive rats," *J. Hypertension*, 12:15–21, 1994.

Bukoski, et al., "Mesenteric artery contractile properties during dietary calcium manipulation in spontaneously hypertensive and Wistar Kyoto normotensive rats," *Am. J. Hypertens.* 2:440–448, 1989.

Bukoski, et al., "Vascular actions of calcium regulating hormones," *Sem. Nephrol.* 15(6):536–549, 1995.

Bukoski, Ishibashi, Bian, "Vascular actions of calcium regulating hormones," *Sem. Nephrol.*, 15(6):536–549, 1995.

Bukoski and McCarron, "Altered aortic reactivity and lowered blood pressure associated with high Ca$^{2+}$-intake in the SHR," *Am. J. Physiol.*, 251:H976–H983, 1986.

Burnstock and Ralevic, "New insights into the local regulation of blood flow by perivascular nerves and endothelium," *Br. J. Plastic Surg.* 47(8):527–543, 1994.

Chen, et al., "Divalent cations suppress 3',5'-adenosine monophosphate accumulation by stimulating a pertussis toxin-sensitive guanine nucleotide-binding protein in cultured bovine parathyroid cells," *Endocrinology*, 123:233–239, 1989.

Cow, D., "Some reactions of surviving arteries," *J. Physiol.*, xlii:125–143, 1911.

Croci, et al., "In vitro characterization of the non-peptide tachykinin NK1 and NK2-receptor antagonists, SR 140333 and SR48968 in different rat and guinea-pig intestinal segments," *Life Sci.* 56:267–275, 1994.

DeWitt, et al., "Endothelium-dependent enhancement of force generation to vasoconstrictors after traumatic brain injury," *J. Neurotrauma*, 11(Suppl. 1), abstract, 1994.

DiPette, et al., "Systemic and regional hemodynamic effects of calcium supplementation in mineralocorticoid-salt induced hypertension," *Hypertension*, 13:77–81, 1989.

Dockray, G. J., "Physiology of enteric neuropeptides;" in: PHYSIOLOGY OF THE GASTROINTESTINAL TRACT 3rd Edition, ed. by L. R. Johnson, Raven Press, NY, pp. 169–209, 1994.

Dominiczak and Bohr, "Cell membrane abnormalities and the regulation of intracellular calcium concentration in hypertension," *Clin. Sci.* 79:415–423, 1990.

Dominiczak and Bohr, "The primacy of membrane microviscosity in genetic hypertension," *Am. J. Hypertension*, 4:963–969, 1991.

Du, et al., "Differential regulation of angiotensin II receptors in rat kidney by low dietary sodium," *Hypertension* 25(2):872–877, 1995.

Dupont and Plummer, "Power and sample size calculations. A review and computer program," *Controlled Clinical Trials*, 11:116–128, 1990.

Edvinsson, et al., "Comparison of peptidergic mechanisms in different parts of the guinea pig superior mesenteric artery: immunocytochemistry at the light and ultrastructural levels and responses in vitro of large and small arteries," *J. Automonic. Nerv. Sys.* 28:141–154, 1989.

Fogh-Anderson, Hedegaard, Thode, Siggard-Andersen, "Sex-dependent relation between ionized calcium in serum and blood pressure," *Clin. Chem.*, 30:116–118, 1984.

Folkow, B., "Physiological aspects of primary hypertension," *Physiol Rev.*, 62:347–504, 1982.

Fox, et al., "A first generation calcimimetic compound (NPS R-568) that acts on the parathyroid cell calcium receptor: a novel therapeutic approach for hyperparathyroidism," *J. Bone Miner. Res.*, 8:S181 (Abstract), 1993.

Frohman, Dush, Martin, "Rapid amplification of full-length cDNAs from rare transcripts: amplification using a single gene-specific oligonucleotide primer," *Proc. Natl. Acad. Sci.*, 85:8998–9002, 1988.

Furchgott and Zawadzki "The obligatory role of endothelium cells in the relaxation of arterial smooth muscle by acetylcholine," *Nature*, 299:373–376, 1980.

Garcia-Palmieri, Costas, Cruz-Vidal, Sorlie, Tillotson, Havlik, "Milk consumption, calcium intake, and decreased hypertension in Puerto Rico," *Hypertension*, 6:322–328, 1984.

Garrett, Capuano, Hammerland, Hung, Brown, Hebert, Nemeth, Fuler, "Molecular cloning and functional expression of human parathyroid calcium receptor cDNAs," *J. Biol. Chem.*, 270:12919–12925, 1995c.

Garrett, et al., "Calcitonin-secreting cells of the thyroid express an extracellular calcium receptor gene," *Endocrinology*, 136:5202–5211, 1995b.

Garrett, et al., "Molecular cloning and functional expression of human parathyroid calcium receptor cDNAs," *J. Biol. Chem.* 270:12919–12925, 1995a.

Gifford, "Approach to the treatment of hypertension," In: *Hypertension Primer*, JL Izzo and HR Black, ed., American Heart Association, Dallas, pp. 285–288 1993.

Gordon, Castelli, Hjortland, Kannel, Dawber, "Diabetes, blood lipids, and the role of obesity in coronary heart risk in women: The Framingham Study," *Ann. Int. Med.*, 87:393–492, 1977.

Grobbee and Hofman, "Effects of calcium supplementation on diastolic blood pressure in young people with mild hypertension," *Lancet Sept.*, 27:703–707, 1986.

Hai and Murphy "Ca$^{2+}$, Cross-bridge Phosphorylation, and Contraction," *Ann. Rev. Physiol.* 51:285–298, 1989.

Harlan, Hull, Schmouder, Landis, Thompson, Larkin, "Blood pressure and nutrition in adults," *Am. J. Epidemiol.*, 120:17–28, 1984.

Hatton and McCarron, "Dietary Calcium and Blood Pressure in Experimental Models of Hypertension. A Reveiw", *Hypertension* 23(4):513–530, 1994.

Hollaway and Bohr, "Reactivity of vascular smooth muscle in hypertensive rats," *Circ. Res.* 33:678–685, 1973.

Holman, M. E. "Membrane Potentials Recorded with High-Resistance Micro-Electrodes; and the Effects of Changes in Ionic Environment on the Electrical and Mechanical Activity of the Smooth Muscle of the Taenia Coli of the Guinea-pig," *J. Physiol. (Lond.)* 141:464–488, 1958.

Holzer, et al., "Sensory neurons mediate protective vasodilation in rat gastric mucosa," *Am. J. Physiol.* 260:G363–G370, 1991.

Ignarro, et al., "EDRF generation and release from perfused bovine pulmonary artery and vein," *Eur. J. Pharmacol* 149:79–88, 1988.

Ishibashi, et al., "Differential expression and effect of calcitriol on myosin in the arterial tree," *Am. J. Physiol: Cell Physiol.* 269:C443–C450, 1995.

Jancso, et al., "Direct evidence for neurogenic inflammation and its prevention by denervation and by pretreatment with capsaicin," *Br. J. Pharmacol.* 31:138–151, 1967.

Jones, A. W., "Altered ion transport in large and small arteries from spontaneously hypertensive rats and the influence of calcium," *Circ. Res.* (Suppl. 1):1177–1182, 1974.

Joshua, et al., "The influence of extracellular $Ca^{2+}$ on microvascular tone in the rat cremaster muscle," *Proc. Soc. Exptl. Biol. Med.* 189:344–352, 1988.

Kageyama and Bravo, "Neurohumoral and hemodynamic responses to dietary calcium supplementation in DOC-salt hypertensive dogs," *Hypertension*, 9:166–170, 1987.

Kitazawa, et aL, "G-protein-mediated $Ca^{2+}$ sensitization of smooth muscle contraction through myosin light chain phosphorylation," *J. Bio. Chem.* 266:1708–1715, 1991.

Kolaj, et al., "The opioid dynorphin modulates AMPA and kainate responses in acutely isolated neurons from the dorsal horn," *Brain Res.* 671:227–244, 1995.

Kotecha and Neild, "Vasodilation and smooth muscle membrane potential changes in arterioles from the guinea-pig small intestine," *J. Physiol.* 482:661–667, 1995.

Li and Duckles, "Effect of age on vascular content of calcitonin gene-related peptide and mesenteric vasodilator nerve activity in the rat," *Eur. J. Pharmacol.*, 236:373–378, 1993.

Li, J., et al., "Physiological changes in extracellular $Ca^{2+}$ modulate endothelium-dependent reactivity of resistance arteries of spontaneously hypertensive and normotensive rats," *Clin. Exp. Hypertens*, 15(5):849–866, 1993.

Lifton, "Molecular genetics of human blood pressure variation," *Science*, 272:676–680, 1996.

Lindskog, et al., "The novel high-affinity antagonist, galantide, blocks the galanin-mediated inhibition of glucose-induced insulin secretion," *Eur. J. Pharmacol.* 210:183–188, 1992.

Maggi and Meli "The sensor-efferent function of capsaicin-sensitive sensory neurons," *Gen. Pharmacol.* 19:1–43, 1988.

Mallette, Bilezikian, Heath, Aurbach, "Primary hyperparathyroidism: clinical and biochemical features," *Medicine*, 53:127–138, 1974.

Massry, Iseki, Campese, "Serum calcium, parathyroid hormone and blood pressure," *Am. J. Nephrol.*, 6:19–28, 1986.

McCarron and Morris, "Blood pressure response to oral calcium in persons with mild to moderate hypertension," *Ann. Int. Med.*, 103:825–831, 1985.

McCarron, D. A., "Is calcium more important than sodium in the pathogenesis of essential hypertension?" *Hypertension* 7:607–627, 1985.

McCarron, Morris, Cole, "Dietary calcium in human hypertension," *Science*, 217:267–269, 1982.

McCarron, Young, Ugoretz, Krutzik, "Disturbances of calcium metabolism in the spontaneously hypertensive rat," *Hypertension*, 3:1152–1167, 1981.

Miller and Scott, "The effect of perivascular denervation on endothelium-dependent relaxation to acteylcholine, *Artery* 17:233–247, 1990.

Missiaen, et al., "Calcium ion homeostasis in smooth muscle," *Pharmac. Ther.* 56:191–231, 1992.

Nemere, et al., "Nontranscriptional effects of steroid hormones," *Receptor* 3:277–291, 1993.

Nemeth and Scarpa, "Cytosolic $Ca^{2+}$ and the regulation of secretion in parathyroid cells," *FEBS Lett.*, 203:15–19, 1986.

Nemeth and Scarpa, "Rapid mobilization of cellular $Ca^{2+}$ in bovine parathyroid cells evoked by extracellular divalent cations. Evidence for a cell surface calcium receptor," *J. Biol. Chem.* 262:5188–5196, 1987.

Nemeth, et al., "$Ca^{2+}$ receptor-dependent regulation of cellular functions," *NIPS* 10:1–5, 1995.

Okamura, et al., "Neurogenic vasodilation in canine uterine and iliac arteries," *J. Hypertension*, 13:1163–1168, 1995.

Pollak, et al., "Mutations in the Human $Ca^{2+}$-sensing receptor gene causes familial hypocalciuric hypercalcemia and neonatal severe hyperparathyfoidism," *Cell* 75(7):1237–1303, 1993.

Racke, et al, "Functional expression of the parathyroid calcium receptor in Xenopus oocytes," *J. Bone Miner. Res.* 6:Suppl:S118, abstract, 1991.

Rapp amd Demg, "Detection and positional cloning of blood presssure quantitative trait loci: is it possible? Identifying the Genes for Genetic Hypertension," *Hypertension* 25(6):1121–1128, 1995.

Resnick, Nicholson, Laragh, "Calcium metabolism and the renin-aldosterone system in essential hypertension," *J. Cardiovasc. Pharmacol.*, 6:S187–S193, 1985a.

Resnick, Sealey, Laragh, "Short and long-term oral calcium alters blood pressure in essential hypertension," *Fed. Proc.*, 44:300, 1985b.

Riccardi, et al., "Cloning and functional expression of a rat kidney extracellular calcium/polyvalent cation-sensing receptor," *Proc. Natl. Acad. Sci.* 92:131–135, 1995.

Rinaldi and Bohr, "Potassium-induced relaxation of arteries in hypertension: modulation by extracellular calcium," *Am. J. Physiol.* 256:H707–H712, 1989.

Rokaeus and Brownstein, "Construction of a porcine adrenal medullary cDNA library and nucleotide sequence analysis of two clones encoding a galanin precursor," *Proc. Natl. Acad. Sci.* 83:6287–6291, 1986.

Ruat, et al., "calcium sensing receptor: molecular cloning in rat and localization to nerve terminals," *Proc. Natl. Acad. Sci.*, 92:3161–3165, 1995.

Rubino, et al., "Prejunctional modulation of sensory-motor nerve mediated vasodilation of the rat mesenteric arterial bed by adenosine," *Eur. J. Pharmacol.* 220:95–98, 1992.

Schmidt-Schoenbein, Zweifach, Kovalcheck, *Microvasc. Res.*, 14:303–317, 1977.

Sharrett and Feinleib, "Water constituents and trace elements in relation to cardiovascular disease," *Prev. Med.*, 4:20–36, 1975.

Shoback, et al., "High calcium and other divalent cations increase inositol trisphosphate in bovine parathyroid cells," *Endocrinology* 123:382–389, 1988.

Strazullo, Siani, Gugliemi, DiCarlo, Galleiit, Cirillo, Mancini, "Controlled trial of long-term oral calcium supplementation in essential hypertension," *Hypertension*, 8:1084–1088, 1986.

Stull, et al, "Vascular smooth muscle contractile elements," *Hypertension* 17:723–732, 1991.

The Fifth Report of the Joint National Committee on Detection, Evaluation, and Treatment of High Blood Pressure (JNC V), *Arch Int. Med.*, 153:154–183, 1993.

Vane, J. R., "The use of isolated organs for detecting active substances in the circulating blood," *Br. J. Pharmacol. Chemother.* 23:360–373, 1964.

Wang and Prewitt, "Captopril reduces aortic and microvascular growth in hypertensive and normotensive rats," *Hypertension*, 15:68–77, 1990.

Wang, et al., "Regulation of PDGF A: A possible mechanism for angiotensin II-induced vascular growth," *Am. J. Physiol.* 269:H356–H364, 1995.

Webb and Bohr, "Mechanism of membrane stabilization by calcium in vascular smooth muscle, *Am. J. Physiol.* 235:C227–C232, 1978.

Wu, et al., "Mechanisms of calcium relaxation of vascular smooth muscle," *Am. J. Physiol.* H1411–H1416, 1991.

Yao, et al., "Heterogeneity of adenovirus-mediated gene transfer in cultured aortic and renal arteries of rats," *Hypertension* 26[part 2]:1056–1050.

Zhang, et al., "Regulation of vascular smooth muscle contraction-myosin light chain phosphorylation dependent and independent pathways," *Can. J. Physiol. Pharmacol.* 72:1386–1391, 1994.

What is claimed is:

1. A method of screening for a compound that reduces vascular tone via a $Ca^{2+}$ receptor of a perivascular sensory nerve comprising:
   (a) contracting a mesenteric artery freed of endothelial tissue and measuring its arterial tension;
   (b) contacting the mesenteric resistance artery with a first compound;
   (c) measuring arterial relaxation of the mesenteric resistance artery after contact with the first compound;
   (d) repeating step (b) but after pre-treatment of the mesenteric resistance artery with a second compound that blocks $Ca^{2+}$ receptor-mediated activity; and
   (e) comparing the levels of arterial tension in step (a) with the levels in step (c), wherein the first compound reduces vascular tone via $Ca^{2+}$ receptor of a perivascular sensory nerve if the level of step (c) is lower than the level of step (a) and if step (d) prevents reduction in arterial tension by the first compound.

2. The method of claim 1, further comprising:
   (f) contacting a mesenteric resistance artery from an animal subject to chronic sensory denervation with the first compound; and
   (g) measuring the level of arterial tension in the mesenteric resistance artery after contact with the first compound.

3. The method of claim 1, wherein the artery is contracted by the addition of norepinephrine.

4. The method of claim 3, wherein the concentration of norepinephrine is 5 mM.

5. The method of claim 2, wherein the chronic sensory denervation is capsaicin-induced.

6. The method of claim 2, wherein the animal is a rat.

* * * * *